(12) United States Patent
Liu et al.

(10) Patent No.: US 10,493,048 B2
(45) Date of Patent: Dec. 3, 2019

(54) THREONATE COMPOUNDS AND METHODS OF USE THEREOF

(71) Applicant: Neurocentria, Inc., Hayward, CA (US)

(72) Inventors: Guosong Liu, Oakland, CA (US); Fei Mao, Fremont, CA (US); Qifeng Sun, Beijing (CN)

(73) Assignee: Neurocentria, Inc., Hayward, CA (US)

( * ) Notice: Subject to any disclaimer, the term of this patent is extended or adjusted under 35 U.S.C. 154(b) by 0 days.

(21) Appl. No.: 15/258,794

(22) Filed: Sep. 7, 2016

(65) Prior Publication Data

US 2017/0128397 A1    May 11, 2017

Related U.S. Application Data

(60) Provisional application No. 62/217,360, filed on Sep. 11, 2015, provisional application No. 62/346,267, filed on Jun. 6, 2016.

(51) Int. Cl.

| | | |
|---|---|---|
| *A61K 31/191* | (2006.01) | |
| *A61K 45/06* | (2006.01) | |
| *A61K 33/06* | (2006.01) | |
| *A61K 31/14* | (2006.01) | |
| *A61K 33/00* | (2006.01) | |
| *A61K 33/26* | (2006.01) | |

(52) U.S. Cl.
CPC ............ *A61K 31/191* (2013.01); *A61K 31/14* (2013.01); *A61K 33/00* (2013.01); *A61K 33/06* (2013.01); *A61K 33/26* (2013.01); *A61K 45/06* (2013.01)

(58) Field of Classification Search
CPC ...... A61K 31/191; A61K 33/06; A61K 33/14; A61K 45/06
See application file for complete search history.

(56) References Cited

U.S. PATENT DOCUMENTS

| | | |
|---|---|---|
| 6,313,170 B1 | 11/2001 | Yu et al. |
| 8,142,803 B2 | 3/2012 | Liu et al. |
| (Continued) | | |

FOREIGN PATENT DOCUMENTS

| | | |
|---|---|---|
| EP | 1038524 | 12/2005 |
| JP | 2014019649 | 2/2014 |
| WO | 2008116226 | 9/2008 |

OTHER PUBLICATIONS

Duman et al., Science 2010, pp. 68-72.*
(Continued)

*Primary Examiner* — Savitha M Rao
(74) *Attorney, Agent, or Firm* — Rudy J. Ng; Kelly A. Tipson; Bozicevic, Field & Francis LLP

(57) ABSTRACT

Provided herein is a method of using threonate to alter cellular physiology, such as neuronal physiology. A method of the present disclosure may include providing to a medium comprising a cell, a threonate-containing compound, or a precursor thereof, to increase the concentration of threonate in the medium, where the increased concentration of threonate is sufficient to increase the concentration of magnesium in the cell. Also provided is a method that includes administering a threonate-containing compound, or a precursor thereof, to an individual, to increase synaptic density in the brain and/or to treat a neurological disorder, e.g., cognitive impairment. The threonate-containing compound of the present disclosure does not include magnesium threonate.

8 Claims, 12 Drawing Sheets

(56) References Cited

U.S. PATENT DOCUMENTS

| | | | |
|---|---|---|---|
| 8,163,301 B2 | 4/2012 | Liu et al. | |
| 8,178,118 B2 | 5/2012 | Liu et al. | |
| 8,178,132 B2 | 5/2012 | Liu et al. | |
| 8,178,133 B2 | 5/2012 | Liu et al. | |
| 8,377,473 B2 | 2/2013 | Liu et al. | |
| 8,470,352 B2 | 6/2013 | Liu et al. | |
| 8,637,061 B2 | 1/2014 | Liu et al. | |
| 8,734,855 B2 | 5/2014 | Liu et al. | |
| 9,125,878 B2 | 9/2015 | Liu et al. | |
| 9,616,038 B2 | 4/2017 | Liu et al. | |
| 2008/0248100 A1* | 10/2008 | Liu | A61K 45/06 424/451 |
| 2008/0249170 A1 | 10/2008 | Liu et al. | |

OTHER PUBLICATIONS

Noraberg et al., (2005) "Organotypic Hippocampal Slice Cultures for Studies of Brain Damage, Neuroprotection and Neurorepair," Current Drug Targets-CNS & Neurological Disorders 4(4): 435-452.
Liu "Efficacy and Safety of MMFS-01, A Synapse Density Enhancer, for Treating Cognitive Impairment in Older Adults: A Randomized, Double-Blind, Placebo-Controlled Trail," Journal of Alzheimer's Disease (2016) 49 971-990.
Slutsky "Enhancement of Learning and Memory by Elevating Brain Magnesium," Neuron (2010) 65: 165-177.
Zhou and Liu "Regulation of density of functional presynaptic terminals by local energy supply," Molecular Brain (2015) 8:42: 1-21.
Duman et al., (2016) "Synaptic plasticity and depression: New insights from stress and rapid-acting antidepressants," Nat Med. 22(3): 238-249.
Karpova et al., (2011) "Fear Erasure in Mice Requires Synergy Between Antidepressant Drugs and Extinction Training," Science 334 (6063): 1731-1734.
Maya-Vetencourt et al., (2008) "The Antidepressant Fluoxetine Restores Plasticity in the Adult Visual Cortex," Science 320: 385-388.
Taylor et al., (2005) "Mechanisms of action of antidepressants: from neurotransmitter systems to signaling pathways."
Duman, RS, (2016) "Synaptic plasticity and depression: new insights from stress and rapid-acting depressants" Nat Med Mar; 22(3): 238-249.
Harrison, Fiona et al., (2009) "Vitamin C function in the brain: vital role of the ascorbate transporter SVCT2" Free Radical Biology and Medicine 46(6)119-730.
Karpova, NN, et al., (2011) "Fear erasure in mice requires synergy between antidepressant drugs and extinction traning" Science 334:1731-1734.
Li, J-Y., et al., (2003) "Huntingtons disease: a synaptopathy?" Trends Mol Med 9:414-420.
Li, Wei et al., (2014) "Elevation of brain magnesium prevents synaptic loss and reverses cognitive deficits in Alzheimer's disease mouse model" Molecular Brain (7):65.
Maya-Vetencourt, JF, et al., (2008) "The antidepressant fluoxetine restores plasticity in the adult visual cortex" Science 320:385-388.
Sun, Qifeng, et al., (2016) "Regulation of structural and functional synapse density by L-threonate through modulation of intraneuronal magnesium concentration" Neuropharmacology (108):426-439.
Scheff, S. W., et al., (2007) "Synaptic alterations in CA1 in mild Alzheimer disease and mild cognitive impairment" Neurology 68(18):1501-1508.
Selkoe, D. J. (2002). "Alzheimer's disease is a synaptic failure" Science 298(5594): 789-791.
Taylor, et al., (2005) "Mechanisms of action of antidepressants: from neurotransmitter systems to signaling pathways" Cell Signal 17(5): 549-557.
Wishart, Thomas, et al., (2006) "Synaptic Vulnerability in Neurodegenerative Disease" J. Neuropathol. Exp. Neurol. 65(8):733-739.

* cited by examiner

Figure 1A
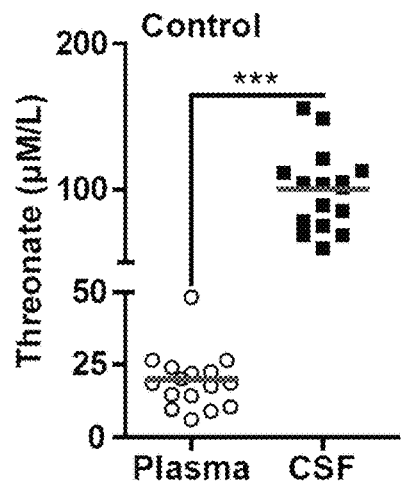
Figure 1B
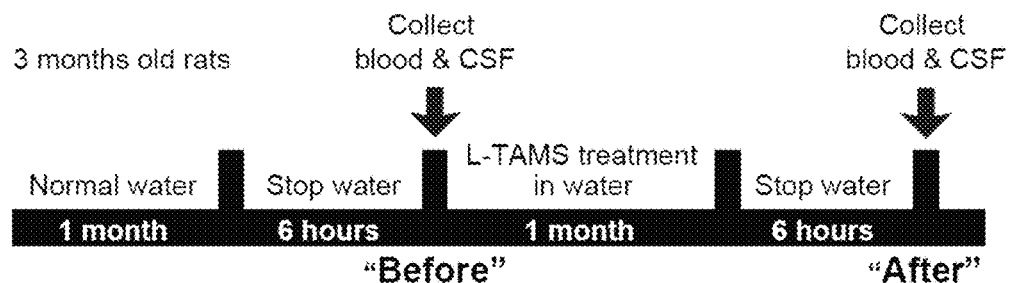
Figure 1C
Figure 1D
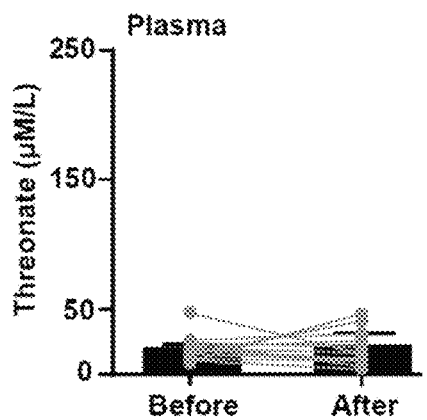
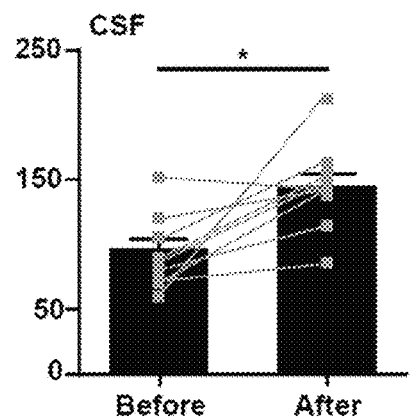

Figure 7Aa
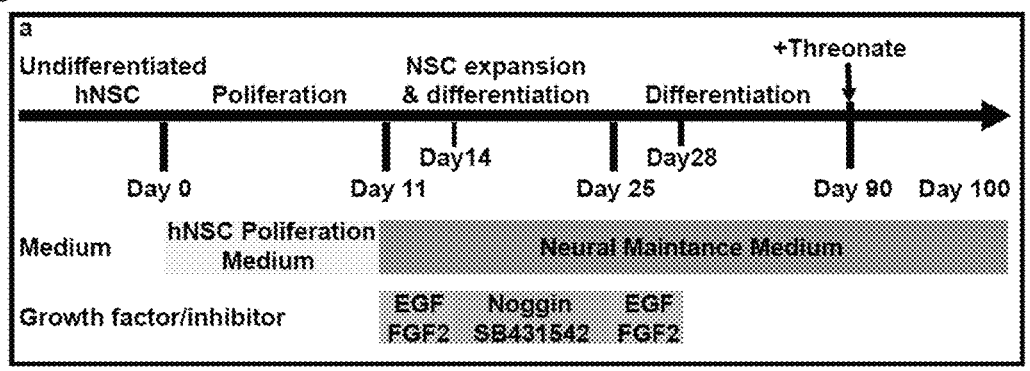
Figure 7Ab
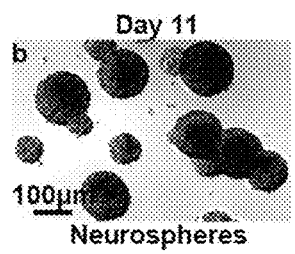
Figure 7Ac
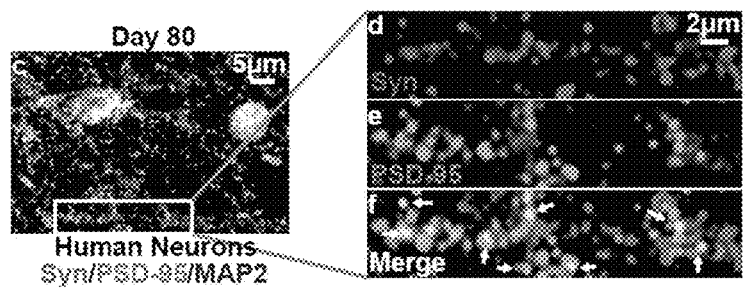
Figure 7Ad
Figure 7Ae
Figure 7Af

THREONATE COMPOUNDS AND METHODS OF USE THEREOF

CROSS-REFERENCE TO RELATED APPLICATIONS

This application claims the benefit pursuant to 35 U.S.C. § 119(e) to U.S. Provisional Patent Application No. 62/217,360, filed Sep. 11, 2015, and U.S. Provisional Patent Application No. 62/346,267, filed Jun. 6, 2016, which applications are incorporated herein by reference in their entirety.

BACKGROUND

Cognitive decline is correlated with brain atrophy associated with synaptic loss. For instance, alteration of synaptic efficacy in the hippocampus is an initial event in cognitive disorders such as Alzheimer's disease (AD). As synapses are the elemental unit of neural computation, the structural and functional loss of synapses are associated with impaired cognition.

Neuronal intracellular ionized $Mg^{2+}$ is an important signaling molecule regulating structural and functional synaptic terminal density, with higher intracellular concentration ($[Mg^{2+}]_i$) generally resulting in greater structural and functional synaptic terminal density. Not only does neuronal intracellular $Mg^{2+}$ promote structural synapse density and plasticity (Slutsky et al., (2010). Neuron 65(2): 165-177), but it also controls whether presynaptic terminals are functional or nonfunctional (Zhou and Liu (2015). Mol Brain 8(1): 42). Functional synapses are able to release neurotransmitters via synaptic vesicles and thus affect the post-synaptic neuron, while nonfunctional synapses are structurally present but fail to release neurotransmitters and are unable to signal to the post-synaptic neuron.

SUMMARY

Methods of using threonate (L-threonate) to alter cellular physiology, such as neuronal physiology, are provided. A method of the present disclosure may include providing to a medium comprising a cell, a threonate-containing compound, or a precursor thereof, to increase the concentration of threonate in the medium, where the increased concentration of threonate is sufficient to increase the concentration of magnesium in the cell. Also provided is a method that includes administering a threonate-containing compound, or a precursor thereof, to an individual, to increase synaptic density in the brain and/or to treat a neurological disorder, e.g., cognitive impairment. The threonate-containing compound of the present disclosure does not include magnesium threonate.

Provided herein is a method for increasing brain synaptic density of an individual by administering to an individual a first dosage form containing a therapeutically effective amount of a threonate-containing compound, or a precursor thereof, to increase synaptic density in one or more regions of the brain of the individual, where the threonate-containing compound, or precursor thereof, is not a magnesium salt.

In any embodiment, the threonate-containing compound, or precursor thereof, may be a monovalent, divalent or trivalent cation salt, or precursor thereof, of threonate. In some embodiments, the monovalent, divalent or trivalent cation is selected from the group consisting of: $H^+$, $Li^+$, $Na^+$, $K^+$, $Ca^{2+}$, $NH_4^+$, $C_1$-$C_8$ monoalkylammonium, $C_2$-$C_8$ dialkylammonium, $C_3$-$C_8$ trialkylammonium, and $Fe^{3+/2+}$.

In any embodiment, the administering may include administering the first dosage form orally, intravenously, or transcutaneously.

In any embodiment, the method may further include co-administering a second dosage form comprising magnesium with the first dosage form.

In any embodiment, the one or more regions of the brain may include the hippocampus, cortex, amygdala, and/or the basal ganglion.

In any embodiment, the first dosage form includes one or more additional agents selected from a pharmacological agent, a flavoring agent, a coloring agent, a sweetening agent, a filling agent, a binding agent, a lubricating agent, an excipient, and a preservative.

Also provided herein is a method of increasing intracellular magnesium concentration, the method including: providing to a medium containing a cell, a threonate-containing compound, or a precursor thereof, to increase the concentration of threonate in the medium, wherein the increased concentration of threonate is sufficient to increase the concentration of magnesium in the cell compared to the concentration of magnesium in the cell before the providing, wherein the threonate-containing compound, or precursor thereof, is not a magnesium salt. In some embodiments, the cell is in vitro, and wherein the providing includes contacting the cell with a composition containing the threonate-containing compound, or a precursor thereof. In some embodiments, the cell is in vivo, and wherein the providing includes administering to an individual, a composition containing the threonate-containing compound, or a precursor thereof, in an amount sufficient to increase the concentration of threonate in an extracellular medium of a cell in the individual. In some embodiments, the concentration of extracellular magnesium in the medium is in the range of 0.3 mM to 2.0 mM. In some embodiments, the concentration of threonate in the medium is 75 µM or more.

Also provided herein is a method of increasing intracellular magnesium concentration, the method including contacting a cell with an effective amount of a glucose transporter (GluT) activator to increase an intracellular magnesium concentration of the cell. In some embodiments, the cell is in vitro. In some embodiments, the contacting includes administering to an individual an effective amount of the GluT activator to increase an intracellular magnesium concentration of the cell in vivo.

In any embodiment, the concentration of magnesium in the cell may be increased by 5% or more.

In any embodiment, the cell may be a cell that expresses a glucose transporter.

In any embodiment, the cell may be a neuronal cell. In some embodiments, the neuronal cell is a central nervous system neuron. In some embodiments, the neuron is a hippocampal or cortical neuron.

Also provided herein is a method of treating a neurological disorder in an individual, the method including: administering to an individual in need of treatment for a neurological disorder, a first dosage form containing a therapeutically effective amount of a threonate-containing compound, or a precursor thereof, to ameliorate the neurological disorder, wherein the threonate-containing compound, or precursor thereof, is not a magnesium salt. In some embodiments, the neurological disorder is caused by insufficient synaptic density and/or insufficient neuron number in one or more brain regions of the individual. In some embodiments, the neurological disorder includes Alzheimer's disease, mild cognitive impairment (MCI), or dementia, Huntingdon's disease, autism, schizophrenia, cognitive decline as secondary effect of disease or medical treatment, depression, dementia, sleep disorder, anxiety, attention deficit hyperactivity disorder (ADHD), migraine, headache, stroke, and neuropathy. In some embodiments, the administering includes administering the first dosage form orally, intravenously, or transcutaneously.

In any embodiment, the method further includes co-administering one or more additional agents with the threonate-containing compound, or precursor thereof. In some embodiments, the one or more additional agents includes one or more of a nutritional active material, a therapeutically active agent, and a locally active agent.

Also provided herein is a kit including: a therapeutic composition containing a therapeutically effective amount of a threonate-containing compound, or a precursor thereof, wherein the threonate-containing compound, or precursor thereof, is not a magnesium salt; and a packaging for holding the therapeutic composition. In some embodiments, the kit further includes a supplemental composition containing magnesium.

BRIEF DESCRIPTION OF THE FIGURES

The skilled artisan will understand that the drawings, described below, are for illustration purposes only. The drawings are not intended to limit the scope of the present teachings in any way.

FIGS. 1A-1D are a collection of graphs and schematic diagrams showing elevation of brain threonate by L-threonic acid magnesium salt (TAMS), according to embodiments of the present disclosure.

DEFINITIONS

Figure 2A:
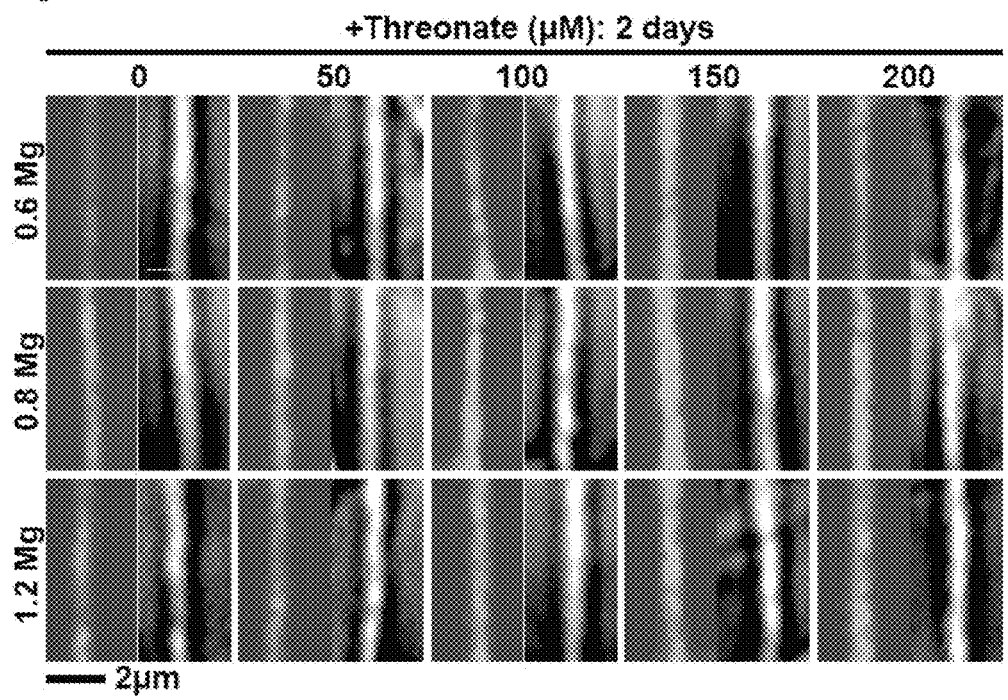
FIGS. 2A-2F are a collection of graphs and images showing that raising extracellular threonate concentration promotes elevation of $[Mg^{2+}]_i$, according to embodiments of the present disclosure.

An "individual" as used herein, may be any suitable animal amenable to the methods and techniques described herein, where in some cases, the individual may be a vertebrate animal, including a mammal, bird, reptile, amphibian, etc. The individual may be any suitable mammal, e.g., human, non-human primate, monkey, rodent, canine, feline, ungulate, etc. In some cases, the individual is a patient, e.g., an individual in need of treatment for a disease. In some cases, the individual is a human.

"Medium", as used herein, may refer to any aqueous solution that is physiologically compatible with a cell that contacts the solution. Where a cell is maintained in vitro, e.g., in culture or a tissue slice, the medium may be any suitable culture medium or buffer solution. Where a cell is in vivo, e.g., in an individual, the medium may be any extracellular fluid (e.g., interstitial fluids, blood plasma or serum, cerebrospinal fluid, etc.), that surrounds or contacts the cell in a tissue.

Generally, the term "cognition" may refer to a process of obtaining, organizing, understanding, processing, and/or using information or knowledge, performed using an individual's mental faculties. Generally, enhancing cognitive function refers to enhancing any aspect of such a process, such as learning, the performance of mental operations, the storage, retrieval, and/or use of information and/or thoughts, memory, and/or preventing a decline of a subjects cognitive state, for example. Various standardized tests may be used to evaluate cognition, cognitive function, and/or cognitive state and may be used to identify a subject who might be conducive to, benefit from, and/or need, maintenance and/or enhancement of same and/or to monitor an effect of treatment relating to same. Examples of suitable tests include the Mini-Mental Status Exam (Folstein, 1975), components of the PROSPER neuropsychological test battery (Houx, 2002), and/or the like. Family history, age, and/or other factors may also be used to identify a subject who might be conducive to, benefit from, and/or need, maintenance and/or enhancement of cognition, cognitive function, and/or cognitive state.

As used herein, the terms "treat," "treatment," "treating," and the like, refer to obtaining a desired pharmacologic and/or physiologic effect. The effect may be prophylactic in terms of completely or partially preventing a health condition, disease or symptoms thereof and/or may be therapeutic in terms of a partial or complete cure for a health condition, disease and/or adverse effect attributable to the health condition or disease. "Treatment," as used herein, covers any treatment of a health condition or disease in a mammal, particularly in a human, and includes: (a) preventing the health condition or disease from occurring in a subject which may be predisposed to the health condition or disease but has not yet been diagnosed as having it; (b) inhibiting the health condition or disease, i.e., arresting its development; and (c) relieving the health condition or disease, e.g., causing regression of the disease, e.g., to completely or partially remove symptoms of the health condition or disease.

A "therapeutically effective amount" or "efficacious amount" means the amount of an agent that, when administered to a cell, a tissue, a mammal or other individual for obtaining a desired change in a physiological parameter, e.g., for treating a disease, is sufficient to effect such desired change, e.g., treatment for the disease or condition. The "therapeutically effective amount" will vary depending on agent, the disease or condition and its severity and the age, weight, etc., of the subject to be treated.

By "pharmaceutically acceptable" is meant a material that is not biologically or otherwise undesirable, i.e., the material may be incorporated into a pharmaceutical composition administered to an individual without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"Co-administer", as used herein, may refer to administering two or more therapeutic agents to an individual to treat a disease. The two or more therapeutic agents may be administered with dosage schedules that are independent of one another (e.g., at different frequencies or intervals of administration). In some cases, two or more therapeutic agents may be administered at the same time, and in some cases, two or more therapeutic agents may be administered at different times (e.g., one before another, in alternating sequence, etc.).

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are described herein.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be described by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present embodiments are not limited in application to the details of construction, the arrangements of components, category selections, weightings, pre-determined signal limits, or the steps set forth in the description or drawings herein. The present teachings are capable of including other embodiments and of being practiced or being carried out in many different ways.

DETAILED DESCRIPTION

As summarized above, disclosed herein are uses of threonate-containing compounds, other than magnesium threonate, to alter cellular physiology, such as neuronal physiology. In general terms, a method of the present disclosure may include providing to a medium comprising a cell, in vivo or in vitro, a threonate-containing compound, or a precursor thereof, to increase the concentration of threonate in the medium. The increase in threonate concentration in the medium may be sufficient (e.g., sufficient concentration of threonate and for a sufficient duration) to bring about a desirable physiological change in the contacted cell. In some cases, the physiological change is an increase in intracellular magnesium concentration. In some cases, the increase in intracellular magnesium concentration underlies one or more other desirable physiological changes in the cell. In some cases, where the cell is a neuronal cell, the physiological change is an increase in the density of synapses, e.g., functional synapses. The present threonate-containing compounds may also be used to treat and/or ameliorate a neurological disorder, such as cognitive impairment and Alzheimer's disease, which are associated with a loss of synaptic density in neurons.

Without wishing to be bound to theory, it is believed that administration of threonate to an individual in a manner that increases the extracellular concentration of threonate in extracellular fluids of tissues, such as in the cerebrospinal fluid (CSF), promotes the uptake of magnesium by cells, e.g., neurons, exposed to the increased extracellular threonate. An increase in the intracellular magnesium concentration as a result of the enhanced uptake of magnesium induced by threonate may contribute to functional changes in the cells and/or the individual, such as an increase in synaptic density in neurons and/or treatment of a neurological disorder, e.g., cognitive impairment.

Further aspects of the present disclosure are now described.

Threonate

Threonate, as used herein, may refer to (2R,3S)-2,3,4-trihydroxybutanoate (L-threonate), represented by formula (I):

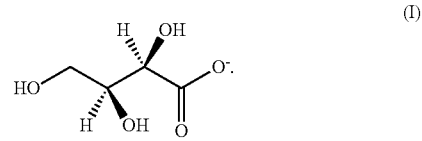

A threonate precursor may include a molecule that can be readily converted to threonate, as a result of ionization, oxidation, reduction, or hydrolysis, etc., with or without the aid of an enzyme, when the composition is dissolved in an aqueous medium or administered to an individual. A suitable threonate precursor may include, without limitation, threonic acid, an ester derivative of threonic acid or threonate (e.g., where one or more hydroxyl groups and/or the carboxylic acid group forms an ester), a lactonized threonic acid (e.g., threonic acid-1,4-lactone), ascorbic acid or a salt thereof, or a derivative thereof, etc.

In some embodiments, the threonate-containing compound is a monovalent, divalent or trivalent cation salt of threonate, represented by the formula (II):

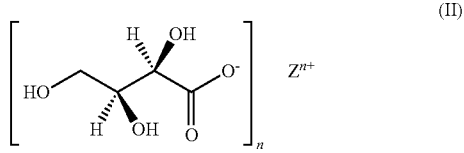

(II)

where $Z^{n+}$ is a cation and n is an integer selected from 1, 2 or 3. The cation, $Z^{n+}$, may be any suitable cation for use in the methods of the present disclosure, with the proviso that the $Z^{n+}$ is not $Mg^{2+}$. Thus, the threonate-containing compound of the present disclosure is not a magnesium salt. Suitable cations include, but are not limited to, e.g., $H^+$, $Li^+$, $Na^+$, $K^+$, $Ca^{2+}$, $NH_4^+$, $C_1$-$C_8$ monoalkylammonium, $C_2$-$C_8$ dialkylammonium, $C_3$-$C_8$ trialkylammonium, and $Fe^{3+/2+}$, etc. In some embodiments, $Z^{n+}$ is $Na^+$. In some embodiments, where the $Z^{n+}$ is a di- or trivalent cation, the anions necessary to balance the charge of $Z^{n+}$ may include a mixture of threonate and another pharmaceutically acceptable anion. By way of example and without limitation, a suitable compound of the invention may be calcium threonate chloride (i.e., Ca[Cl(threonate)]).

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl, ethyl, propyl such as propan-1-yl or propan-2-yl, and butyl such as butan-1-yl, butan-2-yl, 2-methyl-propan-1-yl (iso-butyl) or 2-methyl-propan-2-yl (tert-butyl). In some embodiments, an alkyl group contains from 1 to 8 carbon atoms. In other embodiments, an alkyl group contains from 1 to 6 carbon atoms, such as from 1 to 4 carbon atoms.

The threonate-containing compound, or precursor thereof, of the present disclosure may be used in any suitable composition, formulation or dosage form (e.g., dietary supplement, pharmaceutical composition, etc.), as described further below, for use in a method of the present disclosure described herein. Any composition, formulation or dosage form (e.g., dietary supplement, pharmaceutical composition, etc.) containing the present threonate-containing compound, or precursor thereof, may not include magnesium threonate, or a magnesium-containing precursor thereof. Thus, in cases where a composition, formulation or dosage form (e.g., dietary supplement, pharmaceutical composition, etc.) contains a threonate-containing compound (or a precursor thereof) and a magnesium-containing compound (or a magnesium-containing precursor thereof), the threonate-containing compound (or precursor thereof) and the magnesium-containing compound (or magnesium-containing precursor thereof) may be provided in a manner sufficient to prevent formation of magnesium threonate, or a magnesium-containing precursor thereof in the composition, formulation or dosage form. In some cases, the threonate-containing compound (or precursor thereof) and the magnesium-containing compound (or magnesium-containing precursor thereof) may be physically isolated from each other within the composition by e.g., being in different compartments, such as layers, that are physically isolated from each other; either one or both compounds being coated with a suitable coating, etc.

Methods

Method of Increasing Intracellular Magnesium Concentration

Provided herein is a method of increasing the intracellular concentration of magnesium by increasing the concentration of threonate in a medium containing a cell. The method may include providing to a medium containing a cell, a threonate-containing compound, or a precursor thereof, to increase the concentration of threonate in the medium, where the increased concentration of threonate is sufficient to increase the concentration of magnesium in the cell compared to the concentration of magnesium in the cell before the providing, or compared to the concentration of magnesium in a control cell that has not been provided the threonate-containing compound in a control medium containing the control cell. The threonate-containing compound may be any suitable compound, or a precursor thereof, as described above, with the proviso that the threonate-containing compound is not a magnesium salt.

The medium containing the cell may be any medium that is physiologically compatible with the cell, and may depend on whether the cell of interest is in vitro, e.g., primary cells or cell lines (in, for example, a tissue culture flask, a vial, a tube, a multi-well plate, in a tissue slice, etc.), or in vivo, e.g., cells within a tissue of an individual. The medium may be a suitable culture medium, buffer solution, or extracellular fluid (e.g., interstitial fluids, blood plasma or serum, cerebrospinal fluid, etc.). In embodiments, the present medium includes an amount of magnesium, i.e., extracellular magnesium. "Extracellular magnesium", as used herein, may refer to magnesium that is functionally relevant to the transport of magnesium, from the outside to the inside of the cell. Thus the concentration of extracellular magnesium may be an effective concentration of extracellular magnesium for cellular magnesium influx. The concentration of extracellular magnesium in the medium may be any suitable amount greater than 0.1 mM. In some cases, the concentration of magnesium in the medium is 0.3 mM or more, e.g., 0.4 mM or more, 0.5 mM or more, 0.6 mM or more, 0.7 mM or more, 0.8 mM or more, 0.9 mM or more, 1.0 mM or more, 1.1 mM or more, including 1.2 mM or more, and in some cases may be 5.0 mM or less, e.g., 4.0 mM or less, 3.0 mM or less, 2.0 mM or less, 1.5 mM or less, 1.2 mM or less, 1.0 mM or less, 0.8 mM or less, including 0.7 mM or less. In some embodiments, the concentration of extracellular magnesium in the medium is in the range of 0.3 mM to 5.0 mM, e.g., 0.3 mM to 2.0 mM, 0.4 mM to 1.5 mM, 0.4 mM to 1.2 mM, 0.4 mM to 1.0 mM, including 0.4 mM to 0.8 mM.

The threonate-containing compound may be provided to the medium using any convenient method, and may depend on whether the cell of interest is in vitro, e.g., primary cells or cell lines (in, for example, a tissue culture flask, a vial, a tube, a multi-well plate, in a tissue slice, etc.), or in vivo, e.g., cells within a tissue of an individual. In some cases, a composition containing the threonate-containing compound is contacted with the cell in vitro or added to a medium containing the cell. In some cases, a composition containing the threonate-containing compound is administered to an individual, to increase the concentration of threonate in an extracellular medium of a cell in the individual, as described further below.

The concentration of threonate in the medium may be raised to any suitable concentration sufficient to increase concentration of magnesium in the cell. In some embodiments, the concentration of threonate is raised to 75 µM or more, e.g., 80 µM or more, 85 µM or more, 90 µM or more, 95 µM or more, 100 µM or more, 150 µM or more, including 200 µM or more, and in some cases, to 1,000 µM or less, e.g., 500 µM or less, 300 µM or less, 250 µM or less, including 200 µM or less. In some embodiments, the concentration of threonate is raised to a concentration in the range of 75 µM to 1,000 µM, e.g., 80 µM to 500 µM, 85 µM to 500 µM, 90 µM to 300 µM, including 100 µM to 200 µM.

Where the threonate concentration in a medium containing a cell is increased in vitro, the cell may be present in the medium with increased threonate concentration for any suitable length of time sufficient to increase concentration of magnesium in the cell.

In some cases, the cell is contacted with the medium with increased threonate concentration for 30 min or more, e.g., 60 min or more, 3 hrs or more, 6 hrs or more, 12 hrs or more, 24 hrs or more, including 36 hours or more, and in some cases, for 1 year or less, e.g., 6 months or less, 3 months or less, 1 month or less, 2 weeks or less, 1 week or less, 5 days or less, 3 days or less, including 1 day or less. In some embodiments, the cell is contacted with the medium with increased threonate concentration for a time period in the range of 30 min to 1 year, e.g., 30 min to 6 months, 60 min to 3 months, 60 min to 1 month, 60 min to 1 week, 60 min to 5 days, including 60 min to 3 days.

Where the threonate concentration in a medium containing a cell is increased in vivo, a composition containing the threonate-containing compound, or precursor thereof, may be administered to an individual with a dosing schedule of any suitable duration sufficient to increase the magnesium concentration in the cell. In some embodiments, the composition is administered to an individual with a dosing schedule of 1 month or more, e.g., 2 months or more, 3 months or more, 4 months or more, 5 months or more, 6 months or more, 12 months or more, 2 years or more, 5 years or more, including 10 years or more, and in some embodiments, for 50 years or less, e.g., 25 years or less, 10 years or less, 5 years or less, 1 year or less, including 9 months or less. In some embodiments, the composition is administered to an individual with a dosing schedule in the range of 1 month to 9 months, 3 months to 9 months, 3 months to 1 year, 6 months to 1 year, 12 months to 5 years, 2 years to 5 years, 5 years to 10 years, or 10 years to 50 years. The composition containing the threonate-containing compound may be administered to the individual using any suitable dosage form, dosage regimen or administration route, as described below.

Also provided herein is a method of increasing an intracellular concentration of magnesium of a cell by administering an effective amount of a glucose transporter (GluT) activator to a cell, to increase an intracellular magnesium concentration of the cell. The activator may be any suitable molecule (e.g., small molecule compound; biomolecule, such as a protein, polypeptide, monosaccharide, polysaccharide, nucleic acid, etc.). In some cases, the activator is an agent that increases the intracellular magnesium concentration of the cell in a manner that is sensitive to an inhibitor of a GluT, such as cytochalasin B (CB). In other words, the increase in intracellular magnesium concentration induced by the activator can be inhibited by an amount of inhibitor of GluT, such as CB, that is sufficient to inhibit glucose transport by the GluT. The Glucose transporters of interest include, without limitation, GLUT1, GLUT2, GLUT3, GLUT4, GLUT5, GLUT6, GLUT7, GLUT8, GLUT9, GLUT10, GLUT11, GLUT12, and GLUT13 (corresponding to the Gene ID numbers in, e.g., human of: 6513, 6514, 6515, 6517, 6518, 1182, 155184, 29988, 56606, 81031, 66035, 154091, and 114134, respectively). In some cases, the activator increases the activity of the GluT by 5% or more, e.g., 10% or more, 20% or more, 30% or more, 40% or more, 50% or more, 60% or more, 70% or more, 80% or more, 90% or more, including 100% or more, and in some cases, by 100% or less, e.g., 90% or less, 80% or less, 70% or less, 60% or less, 50% or less, 40% or less, 30% or less, 20% or less, including 10% or less. In some cases, the activator increases the activity of the GluT by from 5% to 10%, from 10% to 20%, from 20% to 30%, from 30% to 40%, from 40% to 50%, from 50% to 60%, from 60% to 70%, from 70% to 80%, from 80% to 90%, or from 90% to 100%.

A cell of the present methods may be any suitable cell, and may be any cell that expresses a glucose transporter (GLUT). The "expression" of a protein, as used herein, may be defined by ascribing at least part of a functional property of the cell to proper expression of the gene encoding the protein (e.g., by pharmacological manipulation, knockdown of expression using inhibitory RNAs, genetic knockouts, etc.) or may refer to detecting the presence of an expression product (e.g., mRNA encoding the protein, via in situ hybridization, reverse transcriptase polymerase chain reaction (RT-PCR), mRNA sequencing, etc.; or the protein itself, via Western blotting, labeling with detectable antibodies, etc.) in the cell at a level above a threshold level (such as a background level). Glucose transporters of interest include, without limitation, GLUT1, GLUT2, GLUT3, GLUT4, GLUT5, GLUT6, GLUT7, GLUT8, GLUT9, GLUT10, GLUT11, GLUT12, and GLUT13 (corresponding to the Gene ID numbers in, e.g., human of: 6513, 6514, 6515, 6517, 6518, 1182, 155184, 29988, 56606, 81031, 66035, 154091, and 114134, respectively) where the cell expressing the glucose transporter is a mammalian cell. In some embodiments, the cell expresses a glucose transporter selected from GLUT1, GLUT2, GLUT3, GLUT4, GLUT6, GLUT8, GLUT10, GLUT13, and combinations thereof. In some cases, the cell expresses GLUT3.

The cells may be somatic cells, stem cells (e.g., embryonic stem cells, adult stem cells, induced pluripotent stem cells (iPSCs)), or cells differentiated from stem cells. In some cases, the cell is, or is derived from, a fibroblast, an oligodendrocyte, a glial cell, a hematopoietic cell, a leukocyte, a neuron, a muscle cell, a bone cell, a hepatocyte, a pancreatic cell, an epithelial cell, a renal cell, an embryonic cell. The cells may be from established cell lines or they may be primary cells, where "primary cells", "primary cell lines", and "primary cultures" are used interchangeably herein to refer to cells and cell cultures that have been derived from an individual and allowed to grow in vitro for a limited number of passages, i.e. splittings, of the culture. For example, primary cultures are cultures that may have been passaged 0 times, 1 time, 2 times, 4 times, 5 times, 10 times, or 15 times, after isolating from an in vivo source, but not enough times to go through the crisis stage. Typically, the primary cell lines are maintained for fewer than 10 passages in vitro. If the cells are primary cells, they may be harvested from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy. In some cases the cells are derived from fetal tissue, e.g., fetal brain tissue, including fetal cortical tissue. In some cases, the cells are derived from stem cells obtained from fetal tissue, e.g., fetal brain tissue, including fetal cortical tissue.

Any suitable cell line may be used in methods of the present disclosure. Cell lines of interest include, without limitation, human embryonic kidney (HEK) cells, Hela cells, PC12, Chinese hamster ovary (CHO) cells, COS cells, etc.

The cell may be in suspension or be attached to a solid support, e.g., a wall of a tissue culture flask. The cell may be isolated, or may be part of an aggregate of cells, e.g., part of an embryo, a tissue, etc.

In some embodiments, the cell is a neuron. The neuron may be any suitable neuron. In some cases, the neuron is a central nervous system (CNS) neuron, e.g., a neuron of the brain, spinal cord, retina, olfactory epithelium, etc. In some embodiments the neuron is, or derived from, a neuron of the hippocampus, cortex, thalamus (including the central thalamus), sensory cortex, ventral tegmental area (VTA), prefontal cortex (PFC), nucleus accumbens (NAc), amygdala, substantia nigra, ventral pallidum, globus pallidus, dorsal striatum, ventral striatum, subthalamic nucleus, dentate gyrus, cingulate gyrus, entorhinal cortex, olfactory cortex, primary motor cortex, and/or cerebellum.

In some embodiments, the cell is a neuronal cell derived from a neuronal stem cell, e.g., a fetal neuronal stem cell. A stem cell may be differentiated into a neuronal cell culturing the stem cell in any suitable differentiation protocol. In some cases, the stem cell is cultured in a neural induction medium to promote differentiation into a neuronal cell. The neural induction medium may include an effective amount of one or more SMAD signaling pathway inhibitors, such as Noggin and SB431542, to promote differentiation into neuronal cells.

The concentration of magnesium in a cell may be increased by the present methods by 5% or more, e.g., 10% or more, 15% or more, 20% or more, 25% or more, 30% or more, 40% or more, including 50% or more, and in some cases, by a factor of 75% or less, e.g., 65% or less, 60% or less, 50% or less, including 50% or less, compared to the concentration of magnesium in the cell before providing the threonate-containing compound to the cell, or compared to the concentration of magnesium in an appropriate control cell. In some cases, the control cell has not been provided the threonate-containing compound in a control medium containing the control cell, where the control medium is otherwise comparable to the medium of the cell provided with the threonate-containing compound. In some embodiments, the concentration of magnesium in a cell is increased by the present method by 5% to 75%, e.g., 10% to 65%, 20% to 60%, including 25% to 50%, compared to the concentration of magnesium in the cell before providing the threonate-containing compound to the cell, or compared to the concentration of magnesium in an appropriate control cell, as described above. The intracellular magnesium concentration may be measured using a suitable method, such as by using a fluorescent magnesium indicator dye (e.g., Magnesium Green™ from Invitrogen) to determine the intracellular magnesium concentration, e.g., by optical estimate, fluorescence detector, etc.

The increase in intracellular magnesium concentration induced by, e.g., contacting, in vitro or in vivo, the cell with a threonate-containing compound, or a precursor thereof, or with a GluT activator, may result in a physiological change in the cell. Where the cell is a neuron, the present method of providing a threonate-containing compound, or a precursor thereof, to the neuron may increase the density of synapses in neurites of the neuron, increase the expression of N-methyl-D-aspartate (NMDA) receptor subunits in the neuron, and/or increase mitochondrial function in the neuron.

In some embodiments, the present methods may increase the density of synapses in the neuron by 5% or more, e.g., 10% or more, 15% or more, 20% or more, 25% or more, 30% or more, 35% or more, including 40% or more, and in some cases, by 75% or less, e.g., 60% or less, 55% or less, 50% or less, 45% or less, including 40% or less, compared to an appropriate control, e.g., the density of synapses in the neuron before the threonate-containing compound or the GluT activator is administered, or the density of synapses in a control neuron in a control medium to which the threonate-containing compound or the GluT activator has not been provided. In some embodiments, the present methods may increase the density of synapses in a region of the brain by from 5% to 75%, e.g., from 10% to 60%, from 10% to 55%, from 15% to 50%, including 20% to 50%, compared to an appropriate control. The density of puncta may be measured, e.g., by measuring the number of fluorescent puncta in processes of neurons across a unit area of neuronal processes, where the neurons are immunostained with one or more antibodies to synaptic proteins (e.g., synaptophysin and/or PSD-95), or are genetically modified to express a detectably labeled (e.g., fluorescently tagged) synaptic protein.

In some cases, the present methods may increase the expression of a N-methyl-D-aspartate (NMDA) receptor subunit involved in synaptic plasticity, e.g., expression of NR2B, in the neuron, by 10% or more, e.g., by 20% or more, by 30% or more, by 40% or more, by 50% or more, by 60% or more, including by 70% or more, and in some cases, by 100% or less, e.g., by 90% or less, by 80% or less, by 70% or less, by 60% or less, including by 50% or less, compared to an appropriate control, e.g., the expression level of the NMDA receptor subunit in the neuron before the threonate-containing compound or the GluT activator is administered, or the expression level of the NMDA receptor subunit in a control neuron in a control medium to which the threonate-containing compound or the GluT activator has not been provided. In some embodiments, the present methods may increase the expression of a NMDA receptor in a region of the brain by from 10% to 100%, e.g., by from 20% to 90%, by from 30% to 80%, including by from 40% to 70%, compared to an appropriate control. The expression level of a NMDA receptor in a region of the brain may be measured, e.g., by performing a Western blot with homogenates of the brain region and probing for the NMDA receptor subunit using an antibody specific to the subunit.

In some embodiments, the present methods may increase mitochondrial function in neurons of a brain region by 10% or more, e.g., 20% or more, 30% or more, 40% or more, 50% or more, 60% or more, including 70% or more, and in some cases, by 100% or less, e.g., 90% or less, 80% or less, 70% or less, 60% or less, including 50% or less, compared to an appropriate control, e.g., the mitochondrial function in the neuron before the threonate-containing compound or the GluT activator is administered, or the mitochondrial function in a control neuron in a control medium to which the threonate-containing compound or the GluT activator has not been provided. In some embodiments, the present methods may increase mitochondrial function in neurons of a brain region by from 10% to 100%, e.g., from 20% to 90%, from 30% to 80%, including from 40% to 70%, compared to an appropriate control. Mitochondrial function in neurons of a region of the brain may be measured, e.g., by measuring the number of mitochondria in the cell, or by measuring aggregation of JC-1 to estimate $\Delta\Psi_m$.

Method of Increasing Brain Synaptic Density or Treating a Neurological Disorder Associated with Synapse Loss Also provided herein is a method of increasing the synaptic density in neuronal tissue of an individual, e.g., an individual suffering from having insufficient synaptic density. The method may include administering a dosage form containing an effective amount of a threonate-containing compound, or a precursor thereof, to increase synaptic density in one or more regions of the brain of the individual, e.g., compared to the density of synapses in the brain regions before the administering. The threonate-containing compound may be any suitable compound or a precursor thereof, as described above, with the proviso that the threonate-containing compound is not a magnesium salt.

Also provided herein is a method of treating (e.g., ameliorating, or preventing or slowing further progression of) a neurological disorder associated with synapse loss, e.g., cognitive impairment, by administering a dosage form containing threonate to an individual in need of a treatment for the neurological disorder, e.g., cognitive impairment. The threonate-containing compound may be any suitable compound or a precursor thereof, as described above, with the proviso that the threonate-containing compound is not a magnesium salt. The dosage form may include threonate in any suitable therapeutic amount to ameliorate the neurological disorder, e.g., cognitive impairment, when administered to the individual.

Neurological disorders that may be treated by administering threonate may be an impairment caused by insufficient synaptic density, reduced synaptic function, and/or insufficient neuron number in a brain region of the individual. The brain region may include, without limitation, the hippocampus, cortex, thalamus (including the central thalamus), sensory cortex, ventral tegmental area (VTA), prefontal cortex (PFC), nucleus accumbens (NAc), amygdala, substantia nigra, ventral pallidum, globus pallidus, dorsal striatum, ventral striatum, subthalamic nucleus, dentate gyrus, cingulate gyrus, entorhinal cortex, olfactory cortex, primary motor cortex, and/or cerebellum. The neurological disorder may include neuropsychiatric and/or neurodegenerative disorders. Neurological disorders that may be treated according to the present methods include, without limitation, mild cognitive impairment (MCI), Alzheimer's disease, Huntingdon's disease, autism, schizophrenia, cognitive decline as secondary effect of disease or medical treatment (HIV disease, cancer, chemotherapy), depression, dementia, sleep disorder, anxiety, attention deficit hyperactivity disorder (ADHD), migraine, headache, stroke, neuropathy, etc.

The individual may be any suitable animal, e.g., a mammal, such as a human, non-human primate, feline, canine, etc. In some cases, the animal is not a rodent, e.g., is not a mouse or a rat. In some cases, the individual is a geriatric individual (e.g., an individual who has lived for 70% or more, e.g., 75% or more, 80% or more, 85% or more, 90% or more, 95% or more, including 98% or more of the average life expectancy). In some cases, the individual is a geriatric human (e.g., an individual who is 65 years old or older, e.g., 70 years old or older, 75 years old or older, 80 years old or older, 85 years old or older, 90 years old or older, including 95 years old or older.

The dosage form may be administered using any suitable route of administration for the dosage form. In some cases, the administration may be oral and/or any other suitable administration, such as transcutaneous, transdermal, intravenous, intramuscular, subdermal, etc. Thus, dosage forms of interest include oral and parenteral dosage forms.

The dosage form may be in any suitable formulation for administering the threonate-containing compound to the individual. Suitable dosage forms include, without limitation, a liquid form, a gel form, a semi-liquid (for example, a liquid, such as a viscous liquid, containing some solid) form, a semi-solid (a solid containing some liquid) form, and/or a solid form, for example. Merely by way of example, a tablet form, a capsule form, a food form, a chewable form, a non-chewable form, a slow- or sustained-release form, a non-slow- or non-sustained-release from (e.g., immediate release form), and/or the like, may be employed. Gradual-release tablets are known in the art. Examples of such tablets are set forth in U.S. Pat. No. 3,456,049, incorporated herein by reference. The dosage form may take the form of a food form, e.g., a food bar, a cereal product, a bakery product, a dairy product, and/or the like. The dosage form may take the form of a bakery form, e.g., a bread-type product, such as a bagel or bread itself, for example, a donut, a muffin, and/or the like.

The present threonate-containing compound, when provided in a liquid form may be used in any suitable manner. In some embodiments, the threonate-containing dosage form may be used as a beverage, such as a milk-based beverage, a sports drink, a fruit juice drink, an alcoholic beverage, and/or the like. In other embodiments, the threonate-containing dosage form in liquid form contains multiple threonate-containing compounds or precursors thereof. In such embodiments, the weight percentage of each threonate-containing compound may vary in relation to the other. In still other embodiments, the threonate-containing dosage form in a liquid form may include water, and a threonate-containing compound, and optionally, at least one agent, such as magnesium-containing compound, sufficient to confer a suitable property to the product. In still another embodiment, a threonate-containing dosage form in a liquid form may be formulated from a dry mix, such as a dry beverage mix or a magnesium-fortified, milk-comprising powder. A dry mix may be suitable in terms of transportation, storage, and/or shelf life. The composition may be formulated from the dry mix in any suitable manner, such as by adding a suitable liquid (e.g., water, milk, fruit juice, alcohol, etc.).

The amount of threonate-containing compound in the dosage form may vary, and may depend on, e.g., the threonate-containing compound, the administration route, the formulation, the administration regimen, the desired outcome, etc. In some embodiments, the threonate component of the threonate-containing compound in a solid oral dosage form (e.g., a pill, tablet, capsule, or like device) is present at 10 mg or more, e.g., 15 mg or more, 20 mg or more, 50 mg or more, 100 mg or more, 200 mg or more, 300 mg or more, 400 mg or more, including 500 mg or more, and in some embodiments, at 1 g or less, e.g., 800 mg or less, 600 mg or less, 400 mg or less, 300 mg or less, 200 mg or less, including 100 mg or less. In some embodiments, the threonate component of the threonate-containing compound in a solid oral dosage form is present at a range of 10 mg to 1 g, e.g., 15 mg to 800 mg, 15 mg to 600 mg, 20 mg to 300 mg, 20 mg to 200 mg, including 200 mg to 100 mg.

In some embodiments, a liquid dosage form of the threonate-containing compound may be formulated to administer the threonate component of the compound at a dose of 10 mg/kg/day or more, e.g., 15 mg/kg/day or more, 20 mg/kg/day or more, 30 mg/kg/day or more, 40 mg/kg/day or more, 50 mg/kg/day or more, 100 mg/kg/day or more, including 500 mg/kg/day or more, and in some embodiments at a dose of 1,000 mg/kg/day or less, e.g., 500 mg/kg/day or less, 300 mg/kg/day or less, 150 mg/kg/day or less, 100 mg/kg/day or less, including 80 mg/kg/day or less. In some cases, the liquid dosage form of the threonate-containing compound may be formulated to administer the threonate component of the compound at a dose of from 10 mg/kg/day to 1,000 mg/kg/day, e.g., from 10 mg/kg/day to 500 mg/kg/day, from 15 mg/kg/day to 300 mg/kg/day, from 15 mg/kg/day to 150 mg/kg/day, including from 20 mg/kg/day to 100 mg/kg/day.

The administration may be performed using any suitable regimen. In some embodiments, a dose of the threonate-containing compound is provided to the individual over the course of one or more administrations, e.g., two administrations or more, three administrations or more, 4 administrations or more, 5 administrations or more, 6 administrations or more, 8 administrations or more, 10 administrations or more, 15 administrations or more, 25 administrations or more, 30 administrations or more, including 50 administrations or more, and in some cases over the course of 1,000 administrations or fewer, e.g., 500 administrations or fewer, 250 administrations or fewer, 100 administrations or fewer, 50 administrations or fewer, 25 administrations or fewer, including 5 administrations or fewer. In some cases, the dose of the threonate-containing compound is provided to the individual over a range of 1 to 5 administrations, 5 to 25 administrations, 25 to 50 administrations, or 50 to 1,000 administrations. In some cases, the administration is self-administration.

In some cases, the dosage form containing the threonate-containing compound is administered to the individual over a time period of 1 month or more, e.g., 2 months or more, 3 months or more, 4 months or more, 5 months or more, 6 months or more, 12 months or more, 2 years or more, 5 years or more, including 10 years or more, and in some embodiments, a time period of 50 years or less, e.g., 25 years or less, 10 years or less, 5 years or less, 1 year or less, including 9 months or less. In some embodiments, the dosage form containing the threonate-containing compound is administered to the individual over a time period in the range of 1 month to 9 months, 3 months to 9 months, 3 months to 1 year, 6 months to 1 year, 12 months to 5 years, 2 years to 5 years, 5 years to 10 years, or 10 years to 50 years.

The dosage form containing the threonate-containing compound may be administered at any suitable time interval. In some cases, the dosage form containing the threonate-containing compound is administered to the individual yearly or more frequently, e.g., monthly or more frequently, weekly or more frequently, daily or more frequently, including hourly or more frequently.

The effective amount of the threonate-containing compound, or a precursor thereof, may be any amount that is sufficient to increase the concentration of threonate in an extracellular medium of the neuronal tissue, e.g., the CSF, relative to the concentration of threonate in the extracellular medium of the neuronal tissue before the administering, for a given administration method. In some embodiments, the threonate concentration in the extracellular medium of the neuronal tissue may increase by 10% or more, e.g., 15% or more, 20% or more, 25% or more, 30% or more, 35% or more, 40% or more, 45% or more, including 50% or more, and in some embodiments, by a factor of 100% or less, e.g., 90% or less, 80% or less, 70% or less, 60% or less, including 50% or less, compared to the concentration of threonate in the extracellular medium of the neuronal tissue before the administering. In some cases, the threonate concentration in the extracellular medium of the neuronal tissue may increase by from 10% to 100%, e.g., from 15% to 90%, from 20% to 80%, from 25% to 70%, including from 30% to 60%, compared to the concentration of threonate in the extracellular medium of the neuronal tissue before the administering.

In some embodiments, the dosage form may include additional agents, such as a pharmacological agent, a flavoring agent, a coloring agent, sweetening agent, a filling agent, a binding agent, a lubricating agent, an excipient, a preservative, a manufacturing agent, and/or the like, merely by way of example, in any suitable form.

In some embodiments, the present method includes co-administering a second dosage form with the first dosage form containing the threonate-containing compound, or precursor thereof. The second dosage form may include an amount of a magnesium-containing compound. Any suitable magnesium compound may be used, with the proviso that the magnesium compound is not magnesium threonate. Suitable magnesium compounds include, e.g., magnesium salt of an amino acid, magnesium acetate, magnesium ascorbate, magnesium citrate, magnesium gluconate, magnesium lactate, magnesium malate, magnesium pyrrolidone carboxylate and magnesium taurate. The second dosage form may be provided in the present method in a manner such that the magnesium containing compound does not physically contact the threonate-containing compound, e.g., when formulated or when administered to an individual. Thus, in some cases, the first dosage form containing the threonate-containing compound and the second dosage form containing the magnesium containing compound may be configured to be administered to an individual or a cell at different times. In some cases, the first dosage form and the second dosage form may be configured to be provided in different compartments that are physically isolated from each other when administered simultaneously to an individual or a cell. In some cases, the first dosage form and/or the second dosage form may be coated with a suitable coating that physically isolates one form the other when administered simultaneously to an individual or a cell. The amount of magnesium in the second dosage form may be any suitable amount. In some embodiments, a second dosage form in the form of a pill, tablet, capsule, or like device, may comprise from about 30 mg to about 200 mg of elemental magnesium. In other embodiments, a second dosage form may contain from about 50 mg to about 100 mg of elemental magnesium associated with the at least one magnesium-containing compound. In still other embodiments, a second dosage form in the form of a food serving, or like dietary serving, may comprise from about 20 mg to about 1 g or even 1.5 g of elemental magnesium. In still other embodiments, a second dosage form in the form of a food serving, or like dietary serving, may comprise from about 50 mg to about 800 mg of elemental magnesium.

A second dosage form appropriate for administration to a subject may be provided in a liquid form, such as one suitable for oral administration, parenteral administration and/or other appropriate routes. Such a composition may comprise any suitable additional agent or agents, whether active or passive. Examples of such agents include water, a sweetening agent, a flavoring agent, a coloring agent, a texturing agent, a stabilizing agent, a preservative, a manufacturing agent, and/or the like, in any suitable form. A component that may negatively affect magnesium bioavailability, such as a phosphate or a polyphosphate, for example, may be avoided. A second dosage form in a liquid form may comprise from about 5 mg/L to about 12 g/L, such as from about 50 mg/L to about 12 g/L, for example, of elemental magnesium associated with the magnesium-containing compound. An amount of from about 50 mg/L to about 3 g/L, such as from about 100 mg/L to about 1.5 g/L, for example, of elemental magnesium associated with the magnesium-containing compound may be suitable for prophylactic application and/or nutritional application. An amount of from about 300 mg/L to about 12 g/L, such as from about 500 mg/L to about 3.5 g/L, for example, of elemental magnesium associated with the magnesium-containing compound may be suitable for therapeutic application.

The first dosage form may be provided in a form that is other than that of the second dosage form. For example, at least one threonate-containing compound may be provided in a solid form, such as solid food or cereal that is taken with a second dosage form in a liquid form, such as a liquid dietary substance. Such administration of dosage forms in multiple forms, may occur simultaneously (e.g., ingesting a threonate tablet with magnesium compound-fortified milk), or at different times.

The co-administration may include any suitable manner of administrating the first and second dosage forms. In some cases, the first and second dosage forms are administered at the same time. In some cases, the first dosage form is administered after the second dosage form, or the second dosage form is administered after the first dosage form. In some cases, the first and second dosage forms are administered in alternating sequence. In some cases, the second dosage form is administered once for every 2 or more, e.g., 3 or more, 4 or more, 5 or more, including 10 or more, and in some cases, every 20 or fewer, e.g., 15 or fewer, 10 or fewer, 8 or fewer, including 5 or fewer administrations of the first dosage form. In some cases, the second dosage form is administered once for every 2 to 20 administrations, e.g., 2 to 15 administrations, 2 to 10 administrations, 2 to 8 administrations, including 2 to 5 administrations of the first dosage form. In some cases, the first dosage form is administered once for every 2 or more, e.g., 3 or more, 4 or more, 5 or more, including 10 or more, and in some cases, every 20 or fewer, e.g., 15 or fewer, 10 or fewer, 8 or fewer, including 5 or fewer administrations of the second dosage form. In some cases, the first dosage form is administered once for every 2 to 20 administrations, e.g., 2 to 15 administrations, 2 to 10 administrations, 2 to 8 administrations, including 2 to 5 administrations of the second dosage form.

In some embodiments, the dosage form containing the threonate-containing compound is a threonate-containing dietary supplement, where the dietary supplement further may not contain magnesium threonate, or a magnesium-containing precursor thereof. In some embodiments, the present dietary supplement contains one or more threonate-containing compounds, or precursors thereof, of the present disclosure and may optionally contain other ingredients generally recognized as safe for food additive use, including, but not limited to, preservatives (e.g., butylated hydroxytoluene, butylated hydroxyanisole), food grade emulsifiers (e.g., lecithin, propylene glycol esters), and pharmaceutically acceptable carriers and excipients (e.g., binders, fillers, lubricants, dissolution aids).

In some embodiments, the present dietary supplement of the present invention is made by combining sodium threonate or other threonate-containing compounds, or precursors thereof, of the present disclosure, as well as any optional components, in the desired relative amounts and mixing the components according to known methods to produce a substantially homogeneous mixture.

In another embodiment, the present dietary supplement may also contain other nutritional active materials including, without limitation, calcium-containing materials such as calcium carbonate, stannol esters, hydroxycitric acid, vitamins, minerals, herbals (e.g., herbal extracts), spices and mixtures thereof. Examples of vitamins that are available as additional ingredients include, but are not limited to, vitamin A (retinol), vitamin D (cholecalciferol), vitamin E group (alpha-tocopherol and other tocopherols), vitamin K group (phylloquinones and menaquinones), thiamine (vitamin $B_1$), riboflavin (vitamin $B_2$), niacin, vitamin $B_6$ group, folic acid, vitamin $B_{12}$ (cobalamins), biotin, vitamin C (ascorbic acid), and mixtures thereof. The amount of vitamin or vitamins present in the final product is dependent on the particular vitamin. Examples of minerals that are available as additional ingredients include, but are not limited to, calcium, magnesium, phosphorus, iron, zinc, iodine, selenium, potassium, copper, manganese, molybdenum and mixtures thereof. In some embodiments, the mineral ingredient is provided in the dietary supplement such that the mineral ingredient is in a separate physical compartment (e.g., separate layer) from the threonate-containing compound such that the mineral ingredient does not physically contact the threonate-containing compound in the dietary supplement. As is the case with vitamins, the amount of mineral or minerals present in the final product is dependent on the particular mineral. It will be clear to one of skill in the art that the present list of additional nutraceutical components are provided by way of example only, and are not intended to be limiting.

In some embodiments, the present dietary supplement is formulated to have suitable and desirable taste, texture, and viscosity for consumption. Any suitable food carrier can be used in the present dietary supplement. Food carriers of the present disclosure include any suitable food product. Examples of such food carriers include, but are not limited to, food bars (granola bars, protein bars, candy bars, etc.), cereal products (oatmeal, breakfast cereals, granola, etc.), bakery products (bread, donuts, crackers, bagels, pastries, cakes, etc.), beverages (milk-based beverage, sports drinks, fruit juices, alcoholic beverages, bottled waters), pastas, grains (rice, corn, oats, rye, wheat, flour, etc.), egg products, snacks (candy, chips, gum, chocolate, etc.), meats, fruits, and vegetables.

For example, liquid food carriers may be used according to the present disclosure to obtain the present dietary supplement in the form of beverages, such as supplemented juices, coffees, teas, and the like. In other embodiments, solid food carriers may be used according to the present disclosure to obtain the present dietary supplement in the form of meal replacements, such as supplemented snack bars, pasta, breads, and the like. In yet other embodiments, semi-solid food carriers may be used according to the present disclosure to obtain the present dietary supplement in the form of gums, chewy candies or snacks, and the like.

In some embodiments, the supplement composition of the present disclosure may be administered in any oral dosage form, including liquid dosage forms (e.g., a suspension or slurry), and oral solid dosage forms (e.g., a tablet or bulk powder). As used herein the term "tablet" refers generally to tablets, caplets, capsules, including soft gelatin capsules, and lozenges.

Tablets are made by methods known in the art and may further include suitable binders, lubricants, diluents, disintegrating agents, colorants, flavoring agents, flow-inducing agents, melting agents which are known in the art. The oral solid dosage form may, optionally, have a film coating to protect the components of the present dietary supplement from one or more of moisture, oxygen and light or to mask any undesirable taste or appearance. Suitable coating agents include, for example, cellulose, hydroxypropylmethyl cellulose. Where desired, tablets can be formulated in sustained release format. Methods of making sustained release tablets are known in the art, e.g., see US2006051416 and US20070065512, both of which are incorporated herein by reference.

In still other embodiments, the threonate-containing compounds, or precursors thereof, of the present disclosure are added to foodstuffs. Such foodstuffs may be naturally high or low in threonate. Other foodstuffs are readily apparent and multiple examples have been described. See, e.g., U.S. Pat. Nos. 6,790,462, 6,261,589, and U.S. patent application Ser. Nos. 10/725,609 and 11/602,126.

In some embodiments, the dosage form containing the threonate-containing compound, or precursor thereof, is a pharmaceutical composition, typically for administration to a person in need of therapeutic levels of threonate, e.g., to treat deficiencies in synaptic density and/or diseases associated therewith. Various delivery systems are known and can be used to administer the threonate-containing compound of the present disclosure, e.g., encapsulation in liposomes, microparticles, microcapsules, etc. Methods of delivery include but are not limited to, intra-arterial, intramuscular, intravenous, intranasal, and oral routes. In some embodiments, the pharmaceutical compositions is delivered locally to the area in need of treatment; this may be achieved by, for example, and not by way of limitation, transdermal patches, local infusion during surgery, by injection, by means of a catheter (with or without an attached pump), or bathing in a solution containing the threonate-containing compound. In some embodiments, the agents are delivered to a subject's nerve systems, preferably the central nervous system.

In some embodiments, administration of a pharmaceutical composition containing the present threonate-containing compound, or precursor thereof, can be effected in one dose, continuously or intermittently throughout the course of treatment. Methods of determining the most effective means and dosage of administration are well known to those of skill in the art and will vary with the composition used for therapy, the purpose of the therapy, the target cell or tissue being treated, and the individual being treated. Single or multiple administrations can be carried out with the dose level and pattern being selected by the treating physician.

For oral administration, the pharmaceutical composition containing the present threonate-containing compound, or precursor thereof, may optionally be formulated by mixing the threonate-containing compound, or precursor thereof, with physiologically or pharmaceutically acceptable carriers that are well known in the art. Such oral dosage forms may be formulated as tablets, pills, dragees, capsules, emulsions, lipophilic and hydrophilic suspensions, liquids, gels, syrups, slurries, suspensions and the like, for oral ingestion by an individual or a patient to be treated.

In one embodiment, the pharmaceutical composition is contained in capsules. Capsules suitable for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. Optionally, the pharmaceutical composition for oral use can be obtained by mixing the threonate-containing compound, or precursor thereof, with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For buccal administration, the pharmaceutical composition may take the form of tablets or lozenges formulated in a conventional manner. For administration by inhalation, the pharmaceutical composition of the present disclosure may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The preparation of pharmaceutical compositions of the present disclosure is conducted in accordance with generally accepted procedures for the preparation of pharmaceutical preparations. See, for example, *Remington's Pharmaceutical Sciences* 18*th Edition* (1990), E. W. Martin ed., Mack Publishing Co., PA. Depending on the intended use and mode of administration, it may be desirable to process further the threonate-containing compound, or precursor thereof, in the preparation of pharmaceutical compositions. Appropriate processing may include mixing with appropriate non-toxic and non-interfering components, sterilizing, dividing into dose units, and enclosing in a delivery device.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or aerosol when used with an appropriate aerosolizer device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

In some embodiments, magnesium supplementation is provided with a pharmaceutical composition containing a threonate-containing compound of the present disclosure, to achieve optimal body magnesium status, by supplementing a person's diet with a magnesium-containing compound. A desired body magnesium status may be defined and/or determined in a variety of ways, including, but not limited to blood magnesium concentration, CSF magnesium concentration, tissue magnesium concentration, intracellular magnesium concentration, and blood cell, e.g., red blood cell, magnesium concentration. Desired body magnesium status may be applicable for general health as well as for specific therapeutic applications described herein (e.g., mild cognitive impairment, AD, depression, osteoporosis, diabetes, etc.). It will be understood that for treatment of different conditions, the optimal body magnesium status may be different to achieve the desired effects.

The pharmaceutical compositions can be formulated in slow release or sustained release forms, whereby a relatively consistent level of the active compound is provided over an extended period. In some embodiments, a threonate-containing compound and/or other therapeutic agents may be administered jointly or separately by using a controlled release dosage form. Controlled release within the scope of this invention can be taken to mean any one of a number of extended release dosage forms. Extended release dosage forms are described in Heaton et al., U.S. Patent Application Pub. No. US2005/0129762 A1 and Edgren et al. U.S. Patent Application Pub. No. 2007/0128279 A1, which are herein incorporated by reference. Time-release formulations are known in the art and are described in Sawada et al. U.S. Patent Application Pub. No. 2006/0292221 A1, which is herein incorporated by reference. The following terms may be considered to be substantially equivalent to controlled release for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, Extended-Release Dosage Forms, 1987 (CRC Press, Inc.). The various controlled release technologies cover a very broad spectrum of drug dosage forms. Controlled release technologies include, but are not limited to, physical systems and chemical systems.

The present disclosure also provides an excipient with the present threonate-containing compound, or a precursor thereof, with or without additional agents, e.g., threonate-containing compound, or precursor thereof, can function as a pharmaceutically acceptable excipient.

In some embodiments of the present disclosure, a threonate-containing compound, or a precursor thereof, can be pressed into pill form without an excipient. In other embodiments, threonate-containing compound, or a precursor thereof, may be combined with a pharmaceutically acceptable lubricant, such as magnesium stearate. In stilt other embodiments, threonate-containing compound, or a precursor thereof, may be combined with other ingredients which affect cognitive functions and/or general health (e.g., vitamins D and E). In still other embodiments, a pill, tablet, dragee, lozenge or other acceptable pharmaceutical form may contain threonate-containing compound, or a precursor thereof, as an excipient and be combined with another agent of choice, including, but not limited to drugs used to treat AD (e.g., cholinesterase inhibitors Aricept, Exelon, Razadine; glutamate regulators—memantine). One of skill in the art will recognize that any number of other pharmaceuticals, nutraceuticals, supplements and other components may be added to the dosage forms herein described where a threonate-containing compound, or a precursor thereof, is used as an excipient.

In some embodiments, microcrystalline cellulose is used as an excipient for direct compression processing. In some embodiments, a wet granulation process will be utilized.

Depending upon the amount and type of drying, the concentration of the threonate-containing compound, or a precursor thereof, in the form of a wet cake and any augmenting agents present, the compressible particles may have different particle sizes, densities, pH, moisture content, etc. One skilled in the art will appreciate that the present threonate-containing compound, or a precursor thereof, may be used in combination with other excipients, including, but not limited to, lactose, microcrystalline cellulose, silicon dioxide, titanium dioxide, stearic acid, starch (corn), sodium starch clycolate, povidone, pregelatinized starch, croscarmellose, ethylcellulose, calcium phosphate (dibasic), talc, sucrose, calcium stearate, hydroxy propyl methylcellulose and shellac (and glaze).

Examples of therapeutically active agents for which improved disintegration results can be obtained include ibuprofen, aldoril, and gemfebrozil, which are relatively high dose (greater than 200 mg/dose) and water-insoluble; verapamil, maxzide, diclofenac and metrolol, which are moderate-dose drug (25-200 mg/dose) and water-soluble; maproltiline, which is moderate dose (25-200 mg/dose) and water-insoluble; triazolam and minoxidil, which are relatively low dose (less than 25 mg/dose) and water-soluble. These examples are provided for discussion purposes only, and are intended to demonstrate the broad scope of applicability of the present disclosure to a wide variety of drugs. It is not meant to limit the scope of the present disclosure in any way.

Surfactants which may be used in the present invention as a compressibility augmenting agent generally include all pharmaceutically-acceptable surfactants. Suitable pharmaceutically-acceptable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate. In some cases, the sodium lauryl sulfate is used as an emulsifying agent in amounts of up to about 0.1% by weight of the formulation.

Alternative anionic surfactants include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the present disclosure amphoteric (amphipathic/amphiphilic surfactants), non-ionic surfactants and/or cationic surfactants are included in the coprocessed compositions of the present disclosure. Suitable pharmaceutically-acceptable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone.

Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives.

Highly polar molecules may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail) which "points away" from the cellulose surface and discourages hydrophilic surface-to-surface cellulose interactions, such as hydrogen-bonding. Preferably, the dye is one which is pharmaceutically acceptable for inclusion in solid dosage forms.

Examples of suitable dyes include Congo Red (chemical name: 3,3'-[[1,1'Biphenyl]-4,4'-diylbis-(azo)]bis[4-amino-1-naphthalenesulfouic acid]disodium salt; FD&C Red No. 40 (also known as "Allura Red") (chemical name: Disodium salt of 6-hydroxy-5[(2-methyl-4-sulfophenyl)azo]-2-naphthalenesulfonic acid); FD&C Yellow No. 5 (common name: tartrazine) (chemical name: 5-oxo-1-(p-sulfophenyl)-4-[(p-sulfophenyl)azo]-2-pyrazoline-3-carboxylic acid, trisodium salt); FD&C Yellow No. 6 (common name: Sunset Yellow FCF) (chemical name: Disodium salt of 1-p-sulphophenylazo-2-naphthol-6-sulfonic acid); Ponceau 4R (chemical name: Trisodium-2-hydroxy-1-(4-sulfonato-1-naphthylazo) naphthalene-6,8-disulfonate); Brown HT (chemical name: Disodium 4,4'-(2,4-dihydroxy-5-hydroxymethyl-3,3-phenylene bisazo)di(napthalene-1-sulfonate)); Brilliant Black BN (Chemical name: Tetrasodium 4-acetamido-5-hydroxy-6-[7-sulfonato-4-(4-sulfonatophenylazo)-1-naphthylazo] naphthalene-1,7-disulfonate); Carmoisine (chemical name: Disodium 4-hydroxy-3-(4-sulfanato-1-naphythylazo) Naphthalene-1-sulfonate); Amaranth (chemical name: Trisodium 2-hydroxy-1-(4-sulfonato-1-naphthylazo) naphthalene-3,6-disulfonate); and mixtures thereof.

Other highly polar molecules which may be utilized as the compressibility augmenting agent include optional additional active agents themselves. For example, it is well-known to those skilled in the art that certain classes of pharmaceuticals, such as anti-pyschotic drugs, are highly polar in nature and may be utilized as a compressibility augmenting agent in accordance with this invention.

The usable concentration range for the selected surfactant depends in part upon not only its molecular weight but also its degree of foaming, particularly when present in agitated slurries which will be spray dried to form the desired particulate. Thus, in those aspects of the present disclosure where surfactants other than sodium lauryl sulfate are coprocessed with the threonate-containing compound, or a precursor thereof, it is to be understood that the surfactant will be present in an amount which enhances the compressibility of the threonate-containing compound, or a precursor thereof, and yet does not have a degree of foaming which would substantially inhibit spray drying.

In an embodiment utilizing a spray-drying process, an aqueous dispersion of threonate-containing compound, or a precursor thereof, and a compressibility augmenting agent (for example, a surfactant or silicon dioxide) is brought together with a sufficient volume of hot air to produce evaporation and drying of the liquid droplets. The highly dispersed slurry is pumpable and capable of being atomized. It is sprayed into a current of warm filtered air, which supplies the heat for evaporation and conveys a dried product to a collecting device. The air is then exhausted with the removed moisture. The resultant spray-dried powder particles may be approximately spherical in shape and may be relatively uniform in size, thereby possessing excellent flowability. The coprocessed particles are not necessarily uniform or homogeneous. Other drying techniques such as flash drying, ring drying, micron drying, tray drying, vacuum drying, radio-frequency drying, and possibly microwave drying, may also be used.

Alternatively, all or part of the excipient may be subjected to a wet granulation with an active ingredient. A representative wet granulation includes loading the novel excipient particles into a suitable granulator, such as those available from Baker-Perkins, and granulating the particles together with the active ingredient, preferably using an aqueous granulating liquid. In some embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with other excipients commonly used by those skilled in the art, depending of course upon the requirements of the particular formulation.

In other embodiments of the present disclosure, a further material is added to the threonate-containing compound, or a precursor thereof, and/or compressibility augmenting agent. Such additional materials include silicon dioxides, non-silicon metal oxides, starches, starch derivatives, surfactants, polyalkylene oxides, cellulose A ethers, celluloses esters, mixtures thereof, and the like. Specific further materials which may be included in the aqueous slurry (and consequently in the resultant agglomerated microcrystalline cellulose excipient) are aluminum oxide, stearic acid, kaolin, polydimethylsiloxane, silica gel, titanium dioxide, diatomaceous earth, corn starch, high amylose corn starch, high amylopectin corn starch, sodium starch glycolate, hydroxylated starch, modified potato starch, mixtures thereof, and the like. These additives may be included in desired amounts, which will be apparent to those skilled in the art.

In addition to one or more active ingredients, additional pharmaceutically acceptable excipients (in the case of pharmaceuticals) or other additives known to those skilled in the art (for non-pharmaceutical applications) can be added to the excipient prior to preparation of the final product. For example, if desired, any generally accepted soluble or insoluble inert pharmaceutical filler (diluent) material can be included in the final product (e.g., a solid dosage form). Such inert pharmaceutical filler may comprise a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, microcrystalline cellulose, mixtures thereof, and the like.

An effective amount of any generally accepted pharmaceutical lubricant, including the calcium or magnesium soaps may optionally be added to the excipient at the time the medicament is added, or in any event prior to compression into a solid dosage form. The lubricant may comprise, for example, magnesium stearate in any amount of about 0.5-3% by weight of the solid dosage form. In embodiments where a surfactant is included as part or all of the compressibility augmenting agent, an additional inclusion lubricant may not be necessary.

The complete mixture, in an amount sufficient to make a uniform batch of tablets, may then subjected to tableting in a conventional production scale tableting machine at normal compression pressures for that machine, e.g., about 1500-10,000 lbs/sq in. The mixture may not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally, rectally. It is contemplated that for certain uses, e.g., antacid tablets, vaginal tablets and possibly implants, that the tablet wilt be larger.

The active agent(s) which may be incorporated with the excipient described herein into solid dosage forms invention include systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, and plant growth stimulants, and the like.

A wide variety of therapeutically active agents can be used in conjunction with the threonate-containing compound, or a precursor thereof, of the present disclosure. The therapeutically active agents (e.g. pharmaceutical agents) which may be used in the compositions of the present disclosure include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenyloin, meprobamate and nitrazepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

A wide variety of locally active agents can be used in conjunction with the excipient described herein, and include both water soluble and water insoluble agents. The locally active agent(s) which may be included in the controlled release formulation of the present invention is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g., metallic salts of fluoride, sodium monofluorophosphate, stannous fluoride, amine fluorides), analgesic agents (e.g., methylsaticylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-inflammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. The solid formulations of the present disclosure may also include other locally active agents, such as flavorants and sweeteners. Generally any flavoring or food additive such as those described in Chemicals Used in Food Processing, pub 1274 by the National Academy of Sciences, pages 63-258 may be used. Generally, the final product may include from about 0.1% to about 5% by weight flavorant.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857-884, hereby incorporated by reference), stabilizers, binders, odor controlling agents, and preservatives.

Alternatively, the excipient can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

In further embodiments of the present disclosure, more than one compressibility augmenting agent is used. Thus, for example, two or more compressibility enhancing agents are used which provide an effect by different mechanisms.

In some embodiments, the present method of administering a threonate-containing compound to an individual may increase the density of synapses in a region of the brain by 5% or more, e.g., 10% or more, 15% or more, 20% or more, 25% or more, 30% or more, 35% or more, including 40% or more, and in some cases, by a factor of 75% or less, e.g., 60% or less, 55% or less, 50% or less, 45% or less, including 40% or less, compared to an appropriate control, e.g., the density of synapses in a comparable region of the brain in a control individual to whom the threonate-containing compound has not been administered. In some embodiments, the present method of administering a threonate-containing compound to an individual may increase the density of synapses in a region of the brain by from 5% to 75%, e.g., from 10% to 60%, from 10% to 55%, from 15% to 50%, including from 20% to 50%, compared to an appropriate control. The density of puncta may be measured, e.g., by measuring the number of fluorescent puncta in processes of neurons across a unit area of neuronal processes, where the neurons are immunostained with one or more antibodies to synaptic proteins (e.g., synaptophysin and/or PSD-95), or are genetically modified to express a detectably labeled (e.g., fluorescently tagged) synaptic protein. In vivo measurements of synaptic density in the brain may be done by, e.g., positron emission tomography (PET) scanning using an appropriate tracer (e.g., $^{18}$F-fludeoxyglucose, (FDG), $^{11}$C-UCB-J or $^{18}$F-UCB-H).

In some cases, the present method of administering a threonate-containing compound to an individual may be sufficient to increase the expression of a N-methyl-D-aspartate (NMDA) receptor subunit involved in synaptic plasticity, e.g., expression of NR2B, in neurons in a region of the brain, by 10% or more, e.g., 20% or more, 30% or more, 40% or more, 50% or more, 60% or more, including 70% or more, and in some cases, by a factor of 100% or less, e.g., 90% or less, 80% or less, 70% or less, 60% or less, including 50% or less, compared to an appropriate control, e.g., the expression level of the NMDA receptor subunit in a comparable region of the brain in a control individual to whom the threonate-containing compound has not been administered. In some embodiments, the present method of administering a threonate-containing compound to an individual may be sufficient to increase the expression of a NMDA receptor in a region of the brain by from 10% to 100%, e.g., from 20% to 90%, from 30% to 80%, including from 40% to 70% compared to an appropriate control. The expression level of a NMDA receptor in a region of the brain may be measured, e.g., by performing a Western blot with homogenates of the brain region and probing for the NMDA receptor subunit using an antibody specific to the subunit.

In some embodiments, the present method of administering a threonate-containing compound to an individual may be sufficient to increase mitochondrial function in neurons of a brain region by 10% or more, e.g., 20% or more, 30% or more, 40% or more, 50% or more, 60% or more, including 70% or more, and in some cases, by 100% or less, e.g., 90% or less, 80% or less, 70% or less, 60% or less, including 50% or less, compared to an appropriate control, e.g., mitochondrial function in neurons from a comparable region of the brain in a control individual to whom the threonate-containing compound has not been administered. In some embodiments, the present method of administering a threonate-containing compound to an individual may be sufficient to increase mitochondrial function in neurons of a brain region by from 10% to 100%, e.g., from 20% to 90%, from 30% to 80%, including from 40% to 70%, compared to an appropriate control. Mitochondrial function in neurons of a region of the brain may be measured, e.g., by measuring the aggregation of JC-1 to estimate $\Delta\Psi_m$.

In some embodiments, the present method of administering a threonate-containing compound to an individual may be sufficient to increase the density of functional neuronal termini in a region of the brain by 5% or more, e.g., 10% or more, 15% or more, 20% or more, 25% or more, including 30% or more, and in some cases, by 40% or less, e.g., 35% or less, 30% or less, 25% or less, including 20% or less, compared to an appropriate control, e.g., the density of functional neuronal termini in a comparable region of the brain in a control individual to whom the threonate-containing compound has not been administered. In some embodiments, the present method of administering a threonate-containing compound to an individual may be sufficient to increase the density of functional neuronal termini in a region of the brain by from 5% to 40%, e.g., 10% to 35%, 10% to 30%, including 10% to 20%, compared to an appropriate control. The density of functional neuronal termini may be measured, e.g., by measuring uptake of an FM dye, e.g., FM1-43, along a unit area of neuronal termini.

Kits

Also provided herein is a kit that includes a therapeutic composition with a therapeutically effective amount of a threonate-containing compound, or a precursor thereof, as described above. The threonate-containing compound may be any suitable compound, or a precursor thereof, as described above, with the proviso that the threonate-containing compound is not a magnesium salt. The present kit may also contain a packaging (e.g., a vial, a blister packaging, a tube, a bag, a box, etc.) for holding the therapeutic composition. A kit of the present disclosure may find use in improving cognitive function and/or reduce cognitive impairment, by administering the threonate-containing compound to an individual.

In some embodiments, the present kit includes a supplemental composition containing a magnesium-containing compound, as described above.

In some embodiments, the present kit includes instructions for using the threonate-containing compound, or a precursor thereof, (e.g., a dosage form or a composition containing the threonate-containing compound, or a precursor thereof) of the present disclosure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

Components of a subject kit can be in separate containers; or can be combined in a single container.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Materials and Methods

Experimental Animals

Male Sprague-Dawley rats were originally purchased from Vital River Laboratory (Animal Technology Co. Ltd., Beijing, China) and bred in Tsinghua University's laboratory animal center. All rats were individually housed in a controlled environment, under an inverted light cycle (light onset at 8:00 p.m. to 8:00 a.m.) and had free access to food and water. On arrival and before the start of the experiments (see below), rats were fed a commercial pelleted diet (Shanghai SLAC Laboratory Animal Co. Ltd), containing normal $Mg^{2+}$ (0.15%) and tap water ad lib. All procedures on rats were approved by Tsinghua University Committee on Animal Care.

Threonate Measurement in Plasma and Cerebral Spinal Fluid (CSF)

To test baseline plasma and CSF threonate concentrations, 3 month old rats were fed deionized water without threonate for 1 month. Water was removed for 6 hr prior to sample collection as a washout period. Then, using the previously describe minimum effective dose of L-threonic acid magnesium salt (L-TAMS) (Neurocentria, Inc., CA, USA) in rats (604 mg/kg/day) (Slutsky et al., 2010), rats were administered either L-TAMS (via deionized drinking water) for 1 month or water only (control). Rat chow for both groups contained basic nutritional $Mg^{2+}$ concentration at 0.15%. Prior to blood and CSF collection, water was removed for 6 hr as a washout period.

To determine threonate concentrations in the plasma and cerebrospinal fluid (CSF), rats were anesthetized with Chloral hydrate (350 mg/kg, i.p.), and then blood and CSF samples were collected from the orbital sinus and cisterna magna, respectively. Blood (0.5-1 ml/rat) and CSF (50-100 μl/rat) samples were collected, centrifuged, and stored at −20° C. until threonate measurement was performed.

Threonate levels in plasma and CSF were determined by high-performance liquid chromatography-tandem mass spectrometry (HPLC-MS/MS, Center of Biomedical Analysis, Tsinghua University) as described previously (Wang et al., 2006. *J Chromatogr B Analyt Technol Biomed Life Sci* 834, 155-162). Briefly, after a simple protein precipitation with methanol, Plasma and CSF samples were centrifuged at 14800 rpm for 15 min, and then the supernatants were collected for analysis. An Eclipse Plus C18 column (4.6×100 mm, 3.5 μm) (Agilent Technologies, Santa Clara, Calif., USA) was employed to separate the analyte. The mobile phase consisted of two solvents: 12.5 mM ammonia, 15 mM ammonium acetate in water (A) and 100% methanol (B). Gradient conditions: 0-2.5 min 90% A/10% B; 2.5-5 min 90-20% A/10-80% B. The flow rate was 0.4 al/min. The Agilent 6460 triple Quadrupole mass spectrometer, equipped with Electrospray Ion Source (ESI) was operated under a negative ionization mode. Multiple reactions monitoring (MRM) transition of m/z 135.1-75.0 was chosen to quantify threonate. Calibration curves were obtained for the following range of threonate concentrations: 10 to 1000 nM/L.

Hippocampal Neuron Cultures

Hippocampal neurons were prepared from postnatal 1 day old rats from Vital River Laboratory and cultured as previous described (Liu et al., 1999. *Neuron* 22, 395-409; Liu et al., 1995. *Nature* 375, 404-408). Following a previously described neuronal culture protocol (Kaech et al., 2006. *Nat Protoc* 1, 2406-2415), and based on the known insulin/insulin-like growth factor concentrations in rat, we added 10 ng/ml insulin (in addition to insulin in B27) into 0.6 mM $[Mg^{2+}]_o$ culture medium. 2 days after plating, cytosine arabinoside (ARA-C, Sigma) was added to a final concentration of 2.5 μM to inhibit glial proliferation. Neurons were plated onto Matrigel® (BD)-coated 8×8 mm coverslips or 6-well cell plates (Corning).

Treatment with Threonate and Other Anions

We used sodium-L-threonate (NaT, Biotium, USA) to study short-term (4 hr) and long-term (2 days) treatment of threonate on mature hippocampal neurons (14-21 days in vitro: DIV). The following anions were used in this study: citrate (200 μM), gluconate (1 mM), malate (5 μM) and glycinate (400 μM) (all from Sigma). The dosage of analogs in culture medium were determined by their known concentrations in vivo (Harrison et al., 2010; Hoffmann et al., 1993; Subramanian et al., 2005). For chemical structure see supplemental FIG. 1.

Intracellular Free $Mg^{2+}$ Analysis $[Mg^{2+}]_i$ was determined by using Magnesium Green™ (MgGreen, Invitrogen). Briefly, neurons were incubated in 2 ml tyrode's buffer (NaCl, 124 mM; KCl, 5 mM; $CaCl_2$, 2 mM; $MgCl_2$, 1 mM; glucose, 30 mM; and HEPES, 25 mM, pH 7.4 with NaOH) with 5 μg MgGreen dissolved for 30 min at 37° C., then washed 3 times, and images were collected using an Olympus IX-70 confocal microscope with the 60× water lens, at a 4× zoom. As described by Zhou (Zhou et al., 2015. *Mol Brain* 8, 42):

$$[Mg^{2+}]_i \propto \frac{F_{(a.u.)}}{D_{diameter}}$$

Where $F_{(a.u.)}$ is the mean fluorescent density (arbitrary units) in the branch of interest which was quantified by using Image-Pro Plus software (IPP, Media Cybernetics, Carlsbad, Calif.), and $D_{diameter}$ is the mean width of the same selected branch in DIC image.

Calculation of Functional Terminal Density by FM1-43 Imaging

The technique to quantify functional terminal density is detailed in Zhou (2015). Briefly, to determine functional presynaptic boutons, mature hippocampal neurons (14-21 DIV) were stained with 10 μM FM1-43 (synaptogreen, Biotium) following physiological pattern of stimulus (6 bursts of 5 APs each at 100 Hz with a 10 s interburst interval), as described by (Slutsky et al., 2004; Zhou and Liu, 2015). Background FM, determined by imaging after unloading of FM dye following 480 APs at 2 Hz, was subtracted from the physiological action potential image. Terminals containing detectable amount of FM after subtraction were considered to be functional.

Fluorescent images were acquired with an Olympus IX-70 confocal microscope with a 60× water lens (numerical aperture=1.2) at a dimension of 78.6×78.6 μm. FM 1-43+ puncta number per $μm^2$ of dendrite was used to estimate functional presynaptic terminal density.

Measurement of Mitochondrial Potential

Mitochondrial transmembrane potential ($\Delta\psi_m$) of hippocampal neurons was observed microscopically (Olympus IX-70) by using 5,5',6,6'-tetrachloro-1,1',3,3'-tetraethylbenzimidazolylcarbocyanine iodide (JC-1, Invitrogen). The monomeric form of JC-1 has an emission maximum at 529 nm. At higher concentrations or potentials the dye forms red fluorescent J-aggregates with an emission maximum of 590 nm. The ratio of J-aggregate/J-monomer is used as an estimate of $\Delta\psi_m$. Mature neurons plated on coverslips were treated with threonate for 2 days, labeled with JC-1 (1 μM)

in tyrode's buffer for 20 min at 37° C., then washed twice with tyrode's buffer, and images were collected at ×180 magnification.

Differentiation of Human Neural Stem Cells to Neurons

Human fetal cortices-derived neural stem cells (hNSC; Angecon, China) were cultured in hNSC medium (Angecon) according to guidelines provided by Angecon. hNSCs were maintained in this medium for 10-14 days, passaged using Accutase (Invitrogen), washed and replated at a dilution of 1:3 to 1:5.

A previously described differentiation protocol was used to differentiate hNSCs to neurons. Briefly, hNSC cultures were dissociated into single cells with Accutase, and then plated on polyornithine/laminin (Sigma)-coated 6-well plates at 50,000 cells per $cm^2$ in neural maintenance medium with EGF (Invitrogen) and FGF2 (Pepro Tech) at a concentration of 10 ng $ml^{-1}$. Neural maintenance medium consists of a 1:1 mixture of DMEM/F12 and Neurobasal medium (Invitrogen), 1×N2 (Invitrogen), 1×B27 (Invitrogen), 1 mM L-glutamine, 0.1 mM non-essential amino acids, 5 µg $ml^{-1}$ insulin, 0.1 mM 2-mercaptoethanol, 25 U $ml^{-1}$ penicillin and 25 mg $ml^{-1}$ streptomycin. After 3-4 days, if the cells reached 95% confluence, culture medium was changed to a neural induction medium, consisting of neural maintenance medium, 500 ng $ml^{-1}$ Noggin (R&D Systems) and 10 µM SB431542 (Tocris). Neurons were maintained 10-14 days in this medium; medium was replaced every day. When neuroepithelial cells appeared, Dispase (Roche) was used to collect cells. They were replated in neural maintenance medium with EGF and FGF2 at 20 ng $ml^{-1}$ for 2-4 days, then changed to neural maintenance medium and cultured for up to 80 days, replacing medium every other day.

Immunocytochemistry

Neuronal cultures were washed three times in 0.01 M PBS followed by fixation for 20 min in 4% paraformaldehyde at 4° C. The neuronal culture coverslips were then washed in PBS before incubation in blocking solution containing 0.1% Triton X-100 and 1% bovine serum albumin for 30 min at room temperature. Then, neurons were incubated with mouse anti-PSD-95 (AB2723, Abcam, 1:100), guinea pig anti-MAP2 (188004, Synaptic Systems, 1:300) and rabbit anti-synaptophysin (MAB5258, Millipore, 1:100) in blocking solution at 4° C. overnight. On the following day, neurons were rinsed with PBS before 2 hr incubation with secondary antibodies including: donkey anti-mouse IgG-CF 488A 1:100, donkey anti-guinea pig IgG-CF 555 1:300 and donkey anti-rabbit IgG-CF 640R 1:200 (Biotium). Finally, neurons were mounted onto slides with anti-fade fluorescent mounting medium (Vector Laboratories) and stored at 4° C. for 2 days.

Quantification of Synaptophysin and PSD-95

Cultures were imaged with a confocal laser inverted microscope (Olympus IX-70) equipped with a 60× (NA 1.2) objective. Each image was collected at a 4× zoom and a resolution of 1024×1024 with a serial z projection of 5 images (thickness of 0.8 µm). The density of synaptophysin (Syn) and PSD-95 was estimated from images by analyzing with IPP. The puncta of Syn and PSD-95, localized at the dendrites labeled by the neuronal marker MAP2, were counted manually. To determine the density of Syn and PSD-95 colocalization, we aligned two sets of images and resulting yellow clusters (Syn: red; PSD-95: green) localized at dendritic were quantified. Fluorescence spots (red and green) having a diameter between 0.1 and 0.6 µm were classified.

Western Blot

Samples of threonate-treated and control hippocampal neurons were solubilized in RIPA buffer (Sigma) containing protease inhibitors (Roche) and phosphatase inhibitors (Roche), then equal amount of proteins were loaded onto 10% polyacrylamide gels. Proteins were transferred to PVDF membranes (Millipore), probed with primary antibodies against Synaptophysin (Millipore), RIM1 and Rab3a (Synaptic System), PSD-95, NR2B, β-tubulin and/or β-actin (all from Cell Signaling Technology) and then followed by an appropriate HRP-coupled secondary antibody (Cell Signaling Technology). The signals were detected by ECL detection reagent (GE Healthcare) and captured on autoradiography film (Kodak). For quantification of protein signals, the integrated optical density (IOD) was measured with IPP, and β-tubulin or β-actin on the same lane served as loading controls.

Statistical Analysis

All data are shown as mean±SEM (standard error of the mean). Statistical significance was determined by two-tailed paired (same coverslips)/unpaired Student's t test or one-way ANOVA followed by Bonferroni's post hoc test. N represents total number of rats, and n represents the total number of separate cultures or coverslips. $P<0.05$ was considered statistically significant.

Example 2: Threonate Treatment Elevates Threonate in the Cerebral Spinal Fluid (CSF)

The distribution of threonate in the body was examined. Similar to previous reports, plasma threonate concentration was approximately 20 µM. Interestingly, in the CSF, threonate concentration was approximately 100 µM, about 5-fold higher than in the periphery ($p<0.001$, FIG. 1A). The effects of oral dosing of L-TAMS (604 mg/kg/day) on the plasma and CSF concentrations of threonate were studied. The change of brain threonate concentrations after oral threonate dosing was measured. Since it takes >2 weeks of L-TAMS treatment to have a noticeable effect on CSF $Mg^{2+}$ concentration and memory function, the concentration of threonate in plasma and CSF after 1 month treatment was monitored (see experimental paradigm, FIG. 1B). Following oral L-TAMS treatment for 1 month, and 6 hour washout, threonate concentration did not change in plasma (FIG. 1C left panel), indicating there was no accumulation in the periphery and that it could be quickly cleared (within 6 hours). In contrast, threonate concentration increased significantly in the CSF by 52% ($p=0.01$, FIG. 1C, right panel). These data indicate that with L-TAMS treatment, threonate accumulated in the CNS compartment, leading to sustained elevation of brain threonate, while in the peripheral compartment threonate did not accumulate.

FIGS. 1A-1C Elevation of Brain Threonate by L-TAMS. (FIG. 1A) Threonate concentrations (µM) in plasma and CSF were determined in 4 month old rats (N=16), fed with normal chow and water. Each circle or square represents an individual rat. (B) Schematic of L-TAMS treatment paradigm. 3 month old rats were treated with normal water for one month, then blood and CSF were collected after a 6 hour washout period ("Before"), which constituted the control samples. Then rats were treated for one month with L-TAMS, blood and CSF samples were collected after a 6 hour washout period ("After"). (C) Threonate concentrations (µM) in the plasma (N=12) and CSF (N=9) were determined before and after 1 month treatment with L-TAMS. The concentration in plasma and CSF for each timepoint is shown for each rat. The average of each group at each timepoint is shown in the histogram behind the individual rat data. Unpaired t test (A), paired t test (C); *p<0.05, ***p<0.001.

Figure 2B:
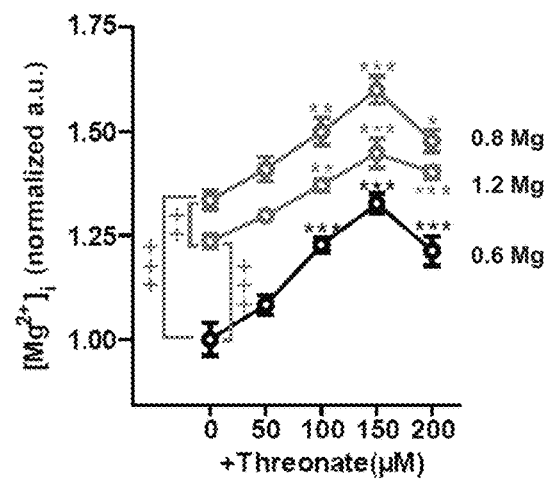
Figure 2C:
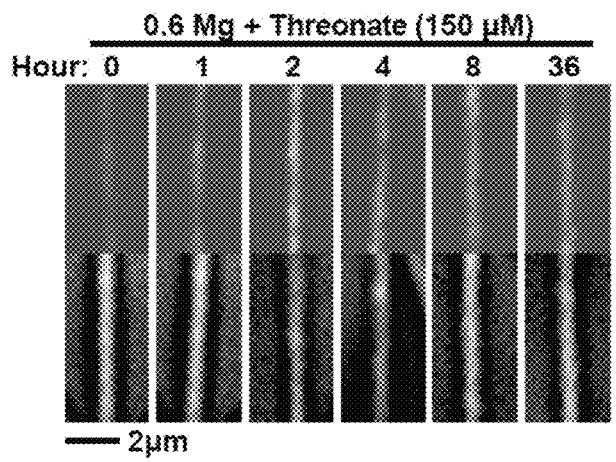
Figure 2D:
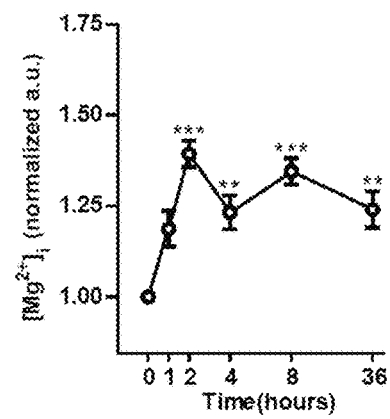

Example 3: Raising Extracellular Threonate Concentration Promoted Elevation of Intracellular Magnesium Concentration The possibility that treatment with threonate would elevate intracellular $[Mg^{2+}]$ in cultured rat hippocampal neurons was tested. First, neurons were cultured for two weeks at physiological extracellular $[Mg^{2+}]$ (0.8 mM or 1.2 mM), or at lower extracellular $[Mg^{2+}]$ (0.6 mM). The latter simulated the lower $Mg^{2+}$ concentration observed in pathophysiological states such as in AD. Intracellular $[Mg^{2+}]$ was quantified by MgGrn fluorescent dye (see methods). Intracellular $[Mg^{2+}]$ was significantly higher at 0.8 and 1.2 mM than at 0.6 mM extracellular $[Mg^{2+}]$ (Unpaired t test, p<0.0001; FIGS. 2A, 2B), and interestingly, intracellular $[Mg^{2+}]$ was significantly higher at 0.8 mM than 1.2 mM extracellular $[Mg^{2+}]$ (Unpaired t test, p<0.01). 2 day treatment with threonate (0-200 µM) induced an increase of intracellular $[Mg^{2+}]$ in a dosage-dependent manner at various extracellular $[Mg^{2+}]$ (0.6 Mg, $F_{4,26}$=19.03, p<0.0001; 0.8 Mg, $F_{4,27}$=12.88, p<0.0001; 1.2 Mg, $F_{4,25}$=17.78, p<0.0001; FIG. 2A, B), up to 150 µM (FIG. 2B). Using the threonate concentration that induced the largest change in intracellular $[Mg^{2+}]$ (150 µM), a time course analysis of the effects of threonate on intracellular $[Mg^{2+}]$ was performed (FIGS. 2C, 2D). Threonate effects were maximal at 2 hr and this increase persisted for the entire course of the experiment ($F_{5,26}$=10.83, p<0.0001; FIG. 2D). Intracellular $[Mg^{2+}]$ following long term treatment (>2 weeks) of threonate was similar to short term threonate treatment.

Figure 2E:
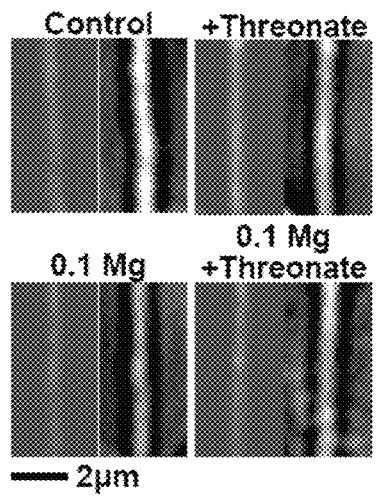
Figure 2F:
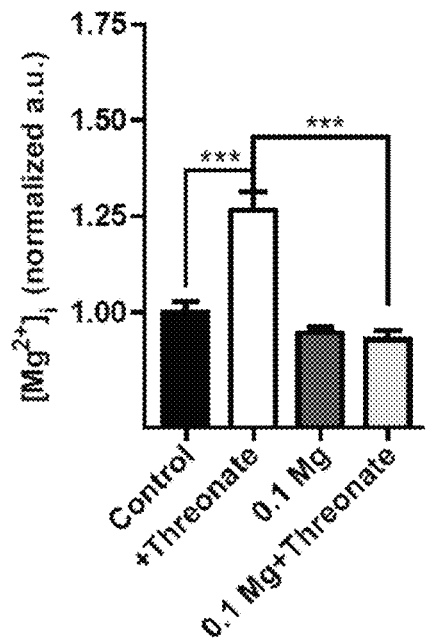

Elevated intracellular $[Mg^{2+}]$ might be due to increased $Mg^{2+}$ influx, reduced $Mg^{2+}$ efflux, and/or release of $Mg^{2+}$ from organelles. To determine the source of the $Mg^{2+}$ contributing to increased $[Mg^{2+}]_i$ by threonate, the effects of threonate when extracellular $[Mg^{2+}]$ was reduced significantly (0.1 mM) was studied. In line with previous experiments, threonate treatment for 4 hr, under 0.6 mM extracellular $[Mg^{2+}]$, induced a significant ~27% increase of intracellular $[Mg^{2+}]$. When extracellular $[Mg^{2+}]$ was reduced to 0.1 mM for 4 hr, there was no noticeable decline in intracellular $[Mg^{2+}]$ (FIGS. 2E, 2F). Interestingly, under such condition, threonate no longer induced elevation of intracellular $[Mg^{2+}]$ (FIG. 2E, F). These results indicate that threonate elevated intracellular $[Mg^{2+}]$ of hippocampal neurons most likely by increasing net flux of $Mg^{2+}$ into the neuron.

FIGS. 2A-2F Raising Extracellular Threonate Concentration Promotes Elevation of $[Mg^{2+}]_i$.

(FIG. 2A) Representative MgGreen (left columns) and DIC (right columns) fluorescent images of individual branches with varying concentrations of $[Mg^{2+}]_o$ (0.6 or 0.8 or 1.2 mM; long-term, LT=2 weeks) and threonate (0-200 µM; 2 days). (FIG. 2B) $[Mg^{2+}]_i$ was calculated as normalized $F_{(a,u)}$ by dividing each branch's MgGreen $F_{(a,u)}$ by its mean diameter (measured from DIC images), from images represented in FIG. 2A. The resulting averages for each $[Mg^{2+}]_o$ and threonate concentration that was tested are displayed. Unpaired t test compared $[Mg^{2+}]_i$ at different $[Mg^{2+}]_o$ (0.6 Mg, n=7; 0.8 Mg, n=8; 1.2 Mg, n=7; ++p<0.01, +++p<0.001). In each group (0.6/0.8/1.2), threonate-treated neurons (n=5-6) were compared to controls, using one-way ANOVA; *p<0.05; p<0.01; *p<0.001. (FIG. 2C) Representative MgGreen (top row) and DIC (bottom row) fluorescent images of individual branches after time course (0-36 hr) of threonate treatment (150 M). (FIG. 2D) Time course line graph of average $[Mg^{2+}]_i$ of neurons (n=4-6); one-way ANOVA and Bonferroni's post hoc test, p<0.01, *p<0.001 versus control (hour 0). (FIG. 2E) Representative MgGreen (left columns) and DIC (right columns) fluorescent images of individual branches after 4 hour treatment with or without threonate (150 µM) in neuronal cultures under 0.6 mM (control) or 0.1 mM (0.1 Mg) $[Mg^{2+}]_o$. (FIG. 2F) Histogram of average $[Mg^{2+}]_i$ calculated from the MgGreen and DIC images represented in E. Unpaired t test compared $[Mg^{2+}]_i$ in control conditions (0.6 Mg; n=10) without threonate to 0.6 Mg with threonate (n=4) and to 0.1 Mg with (n=8) and without (n=8) threonate; ***p<0.001.

Figure 3A:
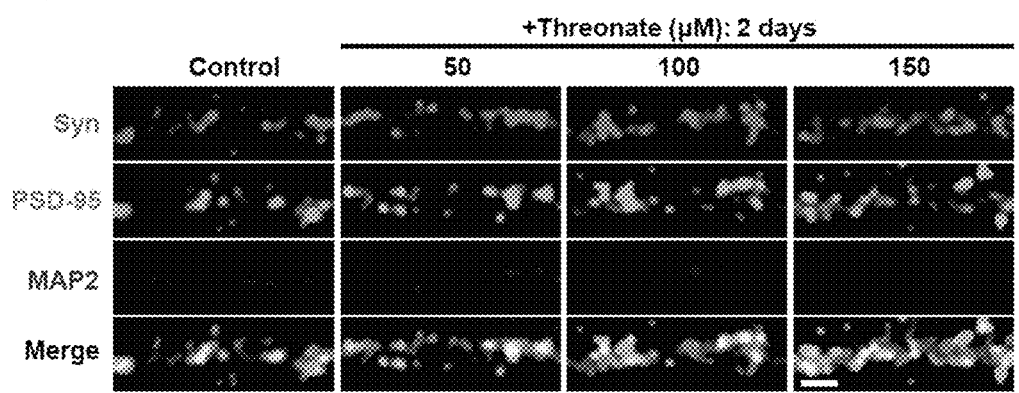
FIGS. 3A-3D are a collection of graphs and images showing enhancement of synaptic density and upregulation of NR2B-containing NMDAR by threonate, according to embodiments of the present disclosure.
Figure 3B:
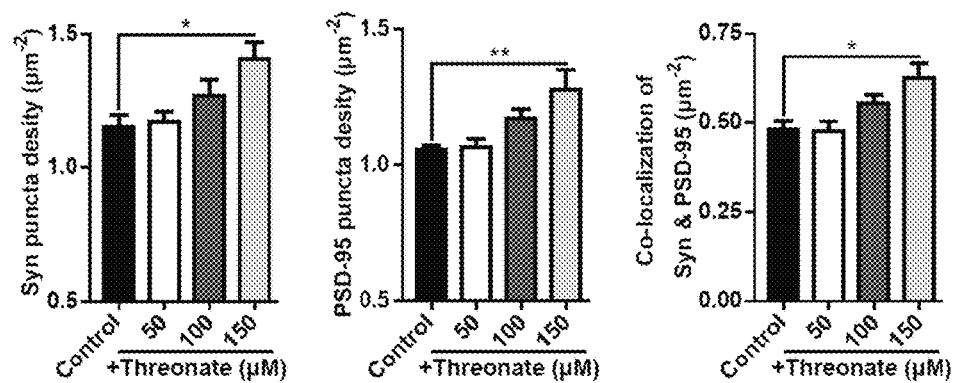

Example 4: Raising Extracellular Threonate Concentration Increases Synaptic Density and Upregulates NR2B-Containing NMDAR Expression The effect of elevation of threonate on synaptic density and plasticity was determined. Presynaptic terminal density was quantified by the density of synaptophysin (Syn) puncta (number per $m^2$) and postsynaptic glutamatergic synapse density was quantified by the density of PSD-95 puncta. Overall synapse density was determined by the colocalization of Syn and PSD-95 expression. Threonate treatment significantly upregulated the density of Syn puncta, PSD-95 puncta, and colocalization of Syn/PSD-95 (Syn, $F_{3,16}$=4.318, p=0.0207; PSD-95, $F_{3,16}$=6.315, p=0.005; Colocalization, $F_{3,16}$=5.653, p=0.0078; FIGS. 3A, 3B).

Figure 3C:
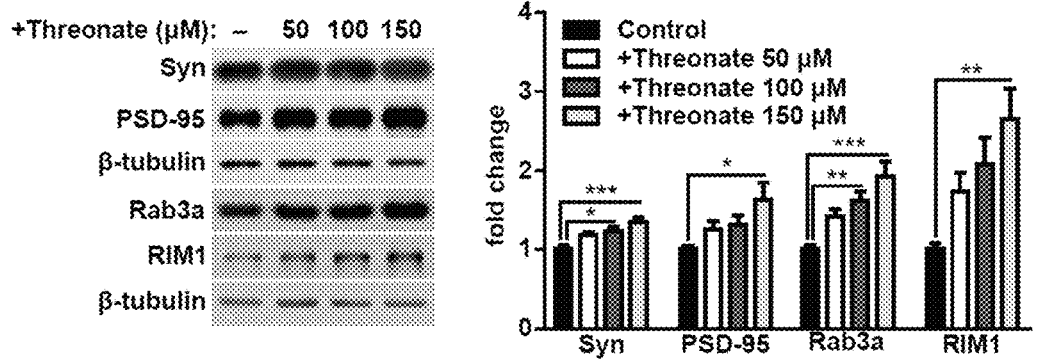

Western blot was used to verify the increase of pre- and postsynaptic proteins in hippocampal neuronal cultures following threonate treatment. After 2 days of threonate treatment, Syn and PSD-95 expression were significantly increased (FIG. 3C). The expression of two presynaptic proteins critical for the functional status of presynaptic terminals, RIM1 and Rab3a, were also checked. Similar to Syn and PSD-95, RIM1 and Rab3a expression were significantly increased following threonate treatment (Syn: $F_{3,37}$=6.849, p=0.0009, n=10-11; PSD-95: $F_{3,36}$=3.350, p=0.0295, n=10; Rab3a: $F_{3,52}$=10.54, p<0.0001, n=14; RIM1: $F_{3,24}$=5.946, p=0.0035, n=7; FIG. 3C).

Figure 3D:
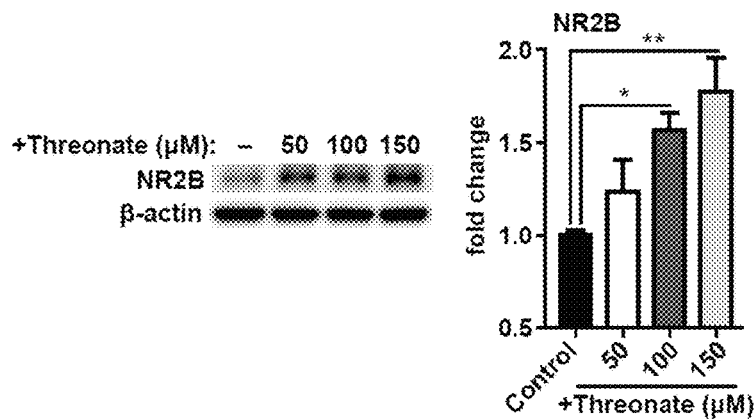

NR2B-containing NMDAR plays an important role in controlling synaptic plasticity. Upregulation of its expression is sufficient to enhance learning and memory ability. Elevation of extracellular $[Mg^{2+}]$ can selectively increase synaptic NR2B-containing NMDAR. Thus, the possibility that threonate treatment can also affect NR2B was tested. Threonate treatment significantly upregulated NR2B-containing NMDAR in hippocampal neurons ($F_{3,17}$=7.493, p=0.0021; FIG. 3D).

Collectively, threonate-treated neurons exhibited higher structural synaptic density, and higher expression of proteins critical for synaptic plasticity.

FIGS. 3a-3d Enhancement of Synaptic Density and Upregulation of NR2B-Containing NMDAR by Threonate.

Hippocampal neuronal cultures were treated with threonate for 2 days. (FIG. 3A) Representative fluorescent images of glutamatergic terminal marker synaptophysin (Syn) and spine marker PSD-95 of controls (n=5) and threonate-treated hippocampal neurons (n=4-6) at varying threonate concentrations (0-150 µM). Scale bar represents 2 µm. (FIG. 3B) Quantification of Syn and PSD-95-immunostained puncta. One-way ANOVA compared density and colocalization of Syn and PSD-95 in threonate-treated neurons to controls; *p<0.05; **p<0.01. (FIG. 3C) Western blot and quantitative analysis of presynaptic proteins RIM1, Rab3a and Syn and postsynaptic protein PSD-95 expression in hippocampal neuronal cultures treated with threonate (0-150 µM). β-tubulin was used as a loading control. Data is represented as fold change relative to control (0 µM threonate). One-way ANOVA and Bonferroni's post hoc test; *p<0.05, p<0.01, *p<0.001; n means number of separate cultures. (FIG. 3D) Same as (FIG. 3C), except western blot is for expression of NR2B-containing NMDAR. β-actin was used as a loading control. One-way ANOVA and Bonferroni's post hoc test; *p<0.05; **p<0.01.

Example 5: Threonate Enhances Mitochondrial Membrane Potential and Increases Functional Presynaptic Terminal Density The effects of threonate on presynaptic terminal function was investigated. If threonate can elevate $[Mg^{2+}]_i$, it might improve the functional status of mitochondria and increase functional terminal density.

Figure 4A:
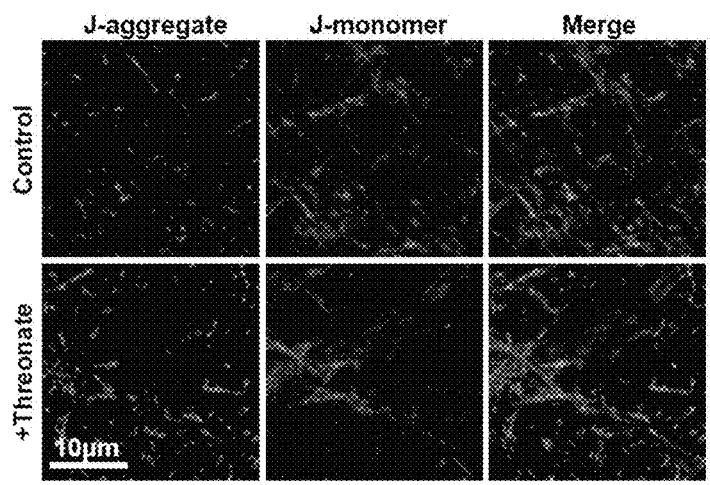
FIGS. 4A-4F are a collection of graphs and images showing that threonate enhances mitochondrial membrane potential and increases functional presynaptic terminal density, according to embodiments of the present disclosure.
Figure 4B:
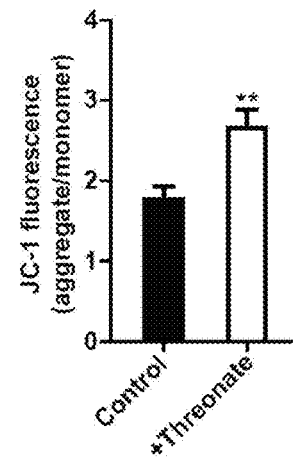

To assess mitochondrial function, their membrane potential ($\Delta\Psi_m$), an important parameter for quantification of mitochondria function, was tested. The ratio of J-aggregate to J-monomer form of JC-1 was used to estimate $\Delta\Psi_m$ (see methods). Addition of threonate for 2 days significantly increased $\Delta\Psi_m$ in hippocampal neurons by 49.6% (Unpaired t test, p<0.01; FIGS. 4A, 4B).

Figure 4C:
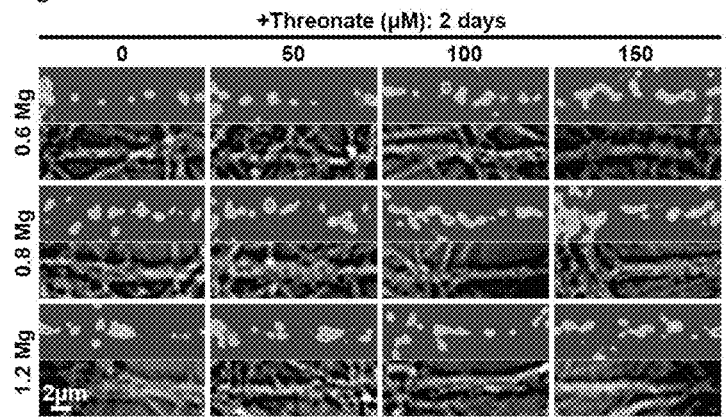
Figure 4D:
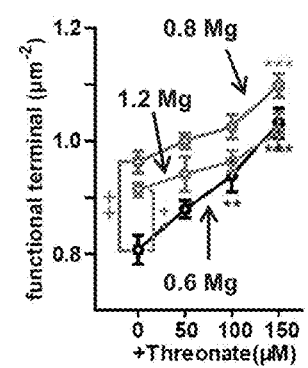

Next, the effects of threonate on functional synapse density was investigated. FM dye was used to evaluate the terminals' ability to undergo activity dependent vesicular turnover. Vesicular endocytosis triggered by stimulation results in FM dye uptake. Terminals labeled by FM as a result of physiological pattern of stimulus are defined as functional (for detailed experimental protocol see Zhou (2015). A similar pattern of change in functional terminal density as with intracellular $[Mg^{2+}]$ in threonate-treated neurons was observed (FIG. 2B). The number of functional terminals was significantly higher at 0.8 and 1.2 mM than 0.6 mM extracellular $[Mg^{2+}]$ (Unpaired t test, p<0.01; FIG. 4A, B), and increased in threonate-treated neurons in a dose-dependent manner under various (0.6, 0.8, or 1.2 mM) conditions (0.6 Mg: $F_{3,21}$=15.15, p<0.0001; 0.8 Mg: $F_{3,16}$=8.946, p=0.001; 1.2 Mg: $F_{3,16}$=3.088, p=0.057; FIGS. 4C, 4D).

Figure 4E:
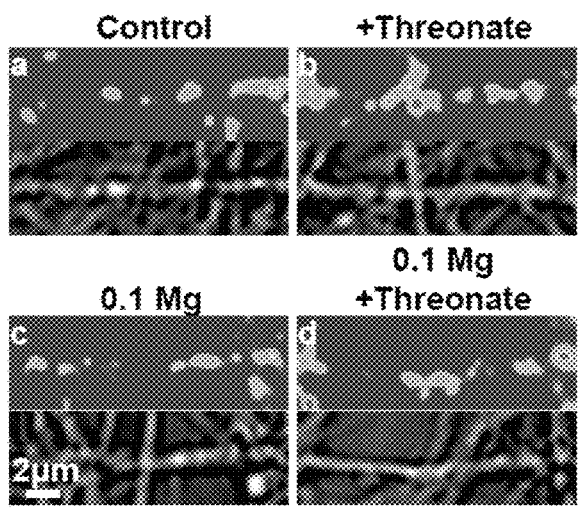
Figure 4F:
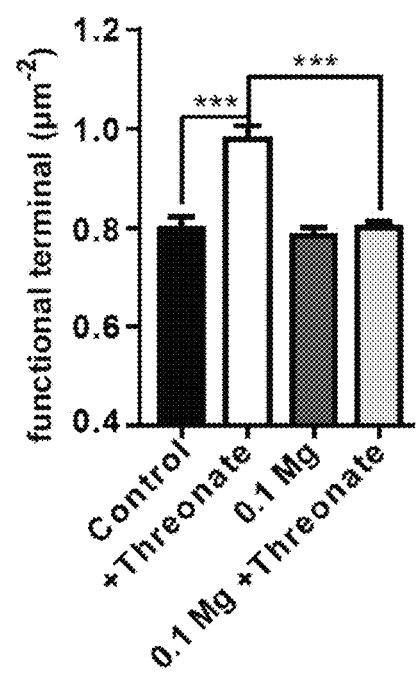

To test whether the increase of functional terminal density by threonate was mediated by elevation of intracellular $[Mg^{2+}]$, the effects of threonate at 0.1 mM extracellular $[Mg^{2+}]$, a condition in which threonate failed to increase intracellular $[Mg^{2+}]$, was investigated (FIG. 2F). Threonate treatment (150 M) for 4 hr induced a significant increase of functional terminal density (by 23%, FIGS. 4Eb, 4F). Reducing extracellular $[Mg^{2+}]$ to 0.1 mM for 4 hr did not reduce functional terminal density (FIGS. 4Ec, 4F) relative to control extracellular $[Mg^{2+}]$ (FIGS. 4Ea, 4F). However, this condition prevented threonate from increasing functional terminal density (FIGS. 4Ed, 4F). These results indicate that elevation of intracellular $[Mg^{2+}]$ may be required for threonate-induced increase of functional terminal density; although, the possibility that threonate promotes functional synapse density independently of $Mg^{2+}$ cannot be ruled out.

FIGS. 4A-4F. Threonate Enhances Mitochondrial Membrane Potential and Increases Functional Presynaptic Terminal Density.

(FIG. 4A) Representative fluorescent images of hippocampal neuronal cultures dyed with 5,5',6,6'-tetrachloro-1,1',3,3'-tetraethyl-benzimidazol-carbocyanine iodide (JC-1) to determine mitochondrial transmembrane potential ($\Delta\Psi_m$) following treatment with threonate (150 M) for 2 days. $\Delta\Psi_m$ was measured by ratio of JC-1 aggregate and monomer. (FIG. 4B) Histogram of average JC-1 aggregate/monomer ratio (Control, 0.6 Mg, n=8; Threonate, n=5). Unpaired t test compared $\Delta\Psi_m$ in threonate-treated neurons to controls; **p<0.01. (FIG. 4C) Mature hippocampal neuronal cultures (14-21 DIV) with varying concentrations of $[Mg^{2+}]_o$ (0.6, 0.8, 1.2 mM) were treated with threonate (0-150 M) for 2 days. Representative fluorescent FM 1-43 (upper row) and DIC (lower row) images following 6*5 AP stimulation protocol of control (0 M threonate) and threonate-treated (50-150 µM threonate) neurons are shown. (FIG. 4D) Functional terminal density was calculated from images represented in FIG. 4C (n=5-7). Unpaired t test compared functional terminal density in 0.6 Mg (n=7), 0.8 Mg (n=5), and 1.2 Mg (n=5) (++p<0.01). In the same $[Mg^{2+}]_o$ group (0.6, 0.8 or 1.2 mM), threonate-treated neurons (50-150 µM; n=5-7) were compared to controls. One-way ANOVA and Bonferroni's post hoc test, p<0.01, *p<0.001. (FIG. 4E) Representative fluorescent FM 1-43 (upper row) and DIC (lower row) images of hippocampal neuronal cultures following treatment with threonate (150 M, 4 hr) or control (0 M threonate) in 0.6 mM $[Mg^{2+}]_o$ (control) or in 0.1 mM $[Mg^{2+}]_o$. (FIG. 4F) Histogram of functional terminal density calculated from images represented in E (n=6). Paired t test compared changes of functional terminal density in 0.6 mM $[Mg^{2+}]_o$ (control) to threonate treatment in control $[Mg^{2+}]_o$ or 0.1 mM $[Mg^{2+}]_o$ with or without threonate treatment; ***p<0.001.

Example 6: Comparison of Effects of Various Anions on Intracellular Magnesium and Functional Synaptic Density The above data suggested that threonate has a direct effect in promoting an increase of intracellular $[Mg^{2+}]$. For elevation of hippocampal neuron $Mg^{2+}$, it was of interest to see whether other major anions have a similar effect. By comparing the molecular structure of compounds that have or do not have this effect, one might be able to ascertain the membrane channel/carrier involved in elevation of intracellular $[Mg^{2+}]$.

Figure 5A:
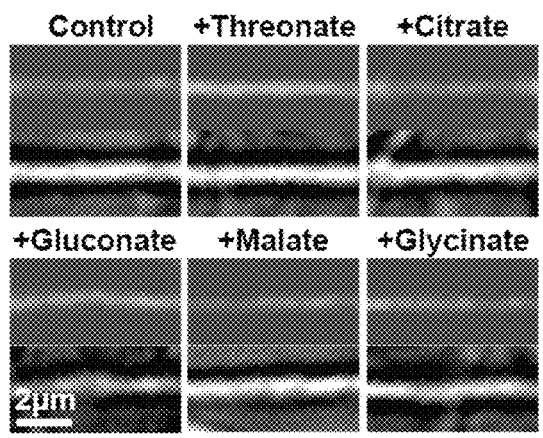
FIGS. 5A-5D are a collection of graphs and images comparing the effects of various anions on $[Mg^{2+}]_i$ and functional synaptic density, according to embodiments of the present disclosure.
Figure 5B:
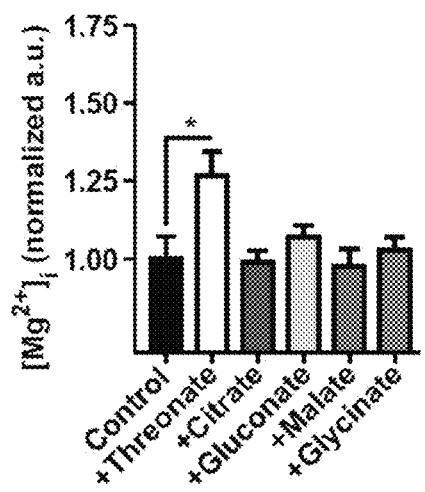
Figure 8:
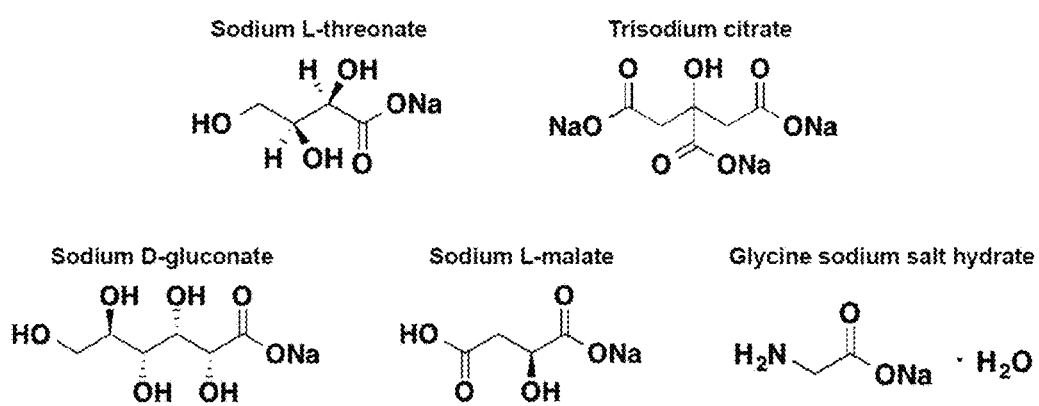
FIG. 8 is a collection of chemical structures representing sodium L-threonate and other compounds.

For comparison, malate, citrate, and gluconate were selected for their structural similarity to threonate as sugar acids (FIG. 8), and glycinate because it is purported to promote cation absorption in periphery. These molecules were tested under 0.6 mM extracellular $[Mg^{2+}]$ conditions, and threonate was the only one able to increase intracellular $[Mg^{2+}]$ ($F_{5,19}$=3.455, p=0.0218; FIGS. 5A, 5B).

Figure 5C:
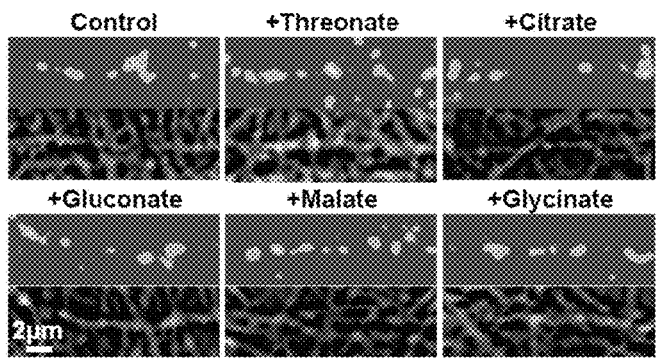
Figure 5D:
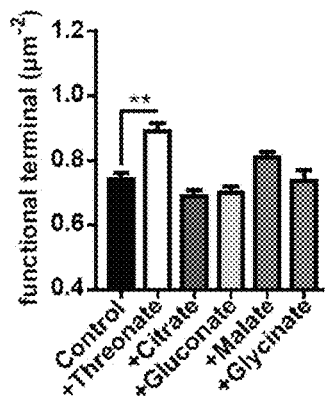

Next, these molecules were compared in their ability to increase functional synapse density in hippocampal neurons. After 2 days of treatment, only threonate was able to significantly increase functional terminal density ($F_{5,25}$=10.99, p<0.0001; FIGS. 5C, 5D). Citrate, gluconate, malate, and glycinate treatments had no significant effects. The fact that only threonate resulted in a change in intracellular $[Mg^{2+}]$ and functional terminal density gave insight into the underlying mechanistic pathway by which threonate enhances synaptic changes.

FIGS. 5A-5D. Comparison of Effects of Various Anions on $[Mg^{2+}]_i$ and Functional Synaptic Density.

(FIG. 5A) Representative MgGreen (upper rows) and DIC (lower rows) fluorescent images of individual branches after 2 day treatment with threonate or threonate analogs under 0.6 mM $[Mg^{2+}]_o$ (control). (FIG. 5B) Histogram of average $[Mg^{2+}]_i$ calculated from the MgGreen and DIC images represented in A. All compound-treated neurons (n=4) were compared to controls (n=5). One-way ANOVA and Bonferroni's post hoc test; *p<0.05. (FIG. 5C) Representative fluorescent FM 1-43 (upper rows) and DIC (lower rows) images of hippocampal neuronal cultures following treatment with threonate or threonate analogs for 2 days in 0.6 mM $[Mg^{2+}]_o$(control). (FIG. 5D) Histogram of functional terminal density calculated from images represented in C (n=5-6). All compound-treated neurons were compared to controls. One-way ANOVA and Bonferroni's post hoc test; **p<0.01.

Example 7: Glucose Transporters (GLUTs) are Necessary for Threonate-Induced Changes and Increase of Functional Synapse Density Since only threonate was effective at increasing intracellular $[Mg^{2+}]$ and functional synaptic density, its transport mechanisms was studied. There are no known transporters for threonate, but because threonate is a derivative of ascorbic acid/dehydroascorbic acid (DHA), it was tested whether threonate acted through ascorbic acid and/or DHA transporters. Ascorbic acid is transported by glucose transporters (GLUTs) and sodium-dependent vitamin C transporter 2 (SVCT2), which are highly expressed in the CNS.

Figure 6A:
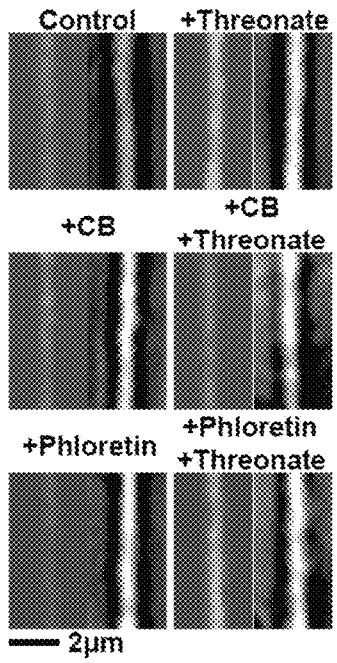
FIGS. 6A-6E are a collection of graphs and images showing that glucose transporters (GLUTs) mediate threonate-induced synaptic changes and increase of functional synapse density, according to embodiments of the present disclosure.
Figure 6B:
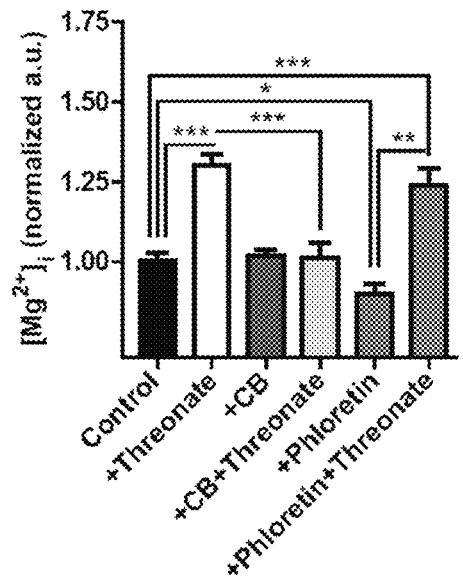

To specifically target GLUTs and SVCT2, cytochalasin B (CB) and phloretin were utilized, because of their ability to inhibit GLUTs and SVCT2, respectively. While short term incubation (4 hr) of hippocampal neuronal cultures with threonate increased intracellular $[Mg^{2+}]$, (by 29.6%, Unpaired t test, p<0.0001), this threonate-mediated increase was prevented by the addition of CB. CB alone did not alter intracellular $[Mg^{2+}]$ relative to control (FIGS. 6A, 6B). In contrast, treatment with phloretin significantly decreased intracellular $[Mg^{2+}]$ relative to placebo (by 10.4%; Unpaired t test, p<0.01), but this reduction was overcome by the addition of threonate. Even in the presence of phloretin, threonate treatment resulted in a significant increase of intracellular $[Mg^{2+}]$ (23.5%, Unpaired t test, p<0.0001) (FIGS. 6A, 6B). These results suggest an involvement of GLUTs, but not SVCT2, in the modulation of intracellular $[Mg^{2+}]$ by threonate which can lead to augmentation of functional terminal density.

Figure 6C:
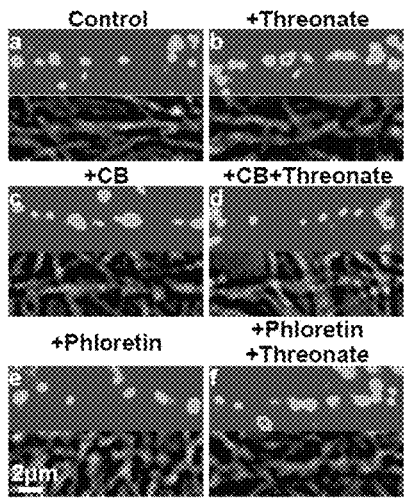
Figure 6D:
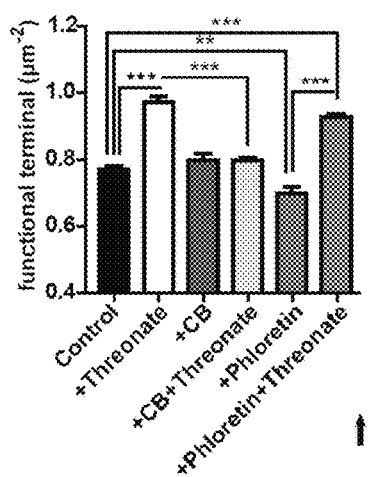
Figure 6E:
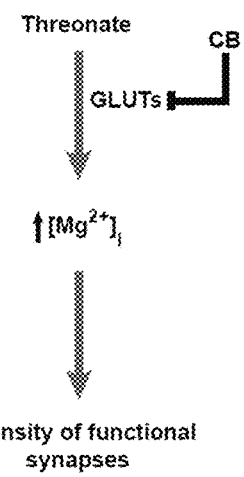

It was the asked whether blocking GLUTs or SVCT2 by CB or phloretin would affect the ability of threonate to elevate functional terminal density of hippocampal neurons. CB treatment alone did not affect the density of functional terminals relative to control; however, in the presence of CB, threonate treatment was unable to elevate functional terminal density (FIGS. 6C, 6D), similar to the effects of CB on threonate-mediated increase of intracellular $[Mg^{2+}]$. In line with the effect of phloretin on intracellular $[Mg^{2+}]$, addition of phloretin significantly decreased functional terminal density (by 10.5%; Unpaired t test, p<0.05) in hippocampal cultures, and was unable to block threonate-mediated increase of functional terminal density relative to control (20.4%; Unpaired t test, p<0.001) (FIGS. 6C, 6D). Altogether, it was concluded that GLUTs mediate threonate-induced increases in neuronal intracellular $[Mg^{2+}]$ and functional synapse density.

FIGS. 6A-6E. Glucose Transporters (GLUTs) Mediate Threonate-Induced Synaptic Changes and Increase of Functional Synapse Density.

Hippocampal cultures were incubated with threonate/cytochalasin B (CB; GLUTs inhibitor)/Phloretin (SVCT2 inhibitor) for 4 hr. (FIG. 6A) Representative MgGreen (left columns) and DIC (right columns) fluorescent images of individual branches following 4 hr treatment with threonate (150 mM) or control (0 mM threonate) with or without CB or Phloretin. (FIG. 6B) $[Mg^{2+}]_i$ was calculated as normalized $F_{(a,u)}$ by dividing each branch's MgGreen $F_{(a,u)}$ by its mean diameter (measured from DIC images), from images represented in A. The resulting averages for each condition (n=4-17) are displayed. Unpaired t test compared $[Mg^{2+}]_i$ in 0.6 mM $[Mg^{2+}]_o$ (control) to threonate treatment in control $[Mg^{2+}]_o$ or CB/Phloretin with or without threonate treatment; *p<0.05; ***p<0.001. (FIG. 6C) Representative fluorescent FM 1-43 (upper rows) and DIC (lower rows) images of hippocampal neuronal cultures following 6*5 AP protocol after threonate (150 μM) or control (0 M threonate) treatment with CB or Phloretin. (FIG. 6D) Histogram of functional terminal density calculated from images represented in C (n=6-15). Unpaired t test compared effect of threonate, CB or Phloretin on functional terminal density to controls, and effect of threonate on functional terminal density in the presence of CB or Phloretin, respectively; p<0.01; *p<0.001. (FIG. 6E) Proposed mechanistic pathway for threonate-induced increase of functional synaptic density Example 8: Threonate Upregulated Expression Level of Syn and PSD-95 in Human Neural Stem Cell-Derived Neurons To help understand the potential ramifications of the present study in human, the effects of threonate on synaptic changes in human stem cell-derived neurons were examined. In a separate study, it was found that plasma threonate concentrations were similar between human and rat; but human CSF threonate of concentrations, of 100-300 μM, were much higher than those in rat (internal observation). Threonate function may vary between rodent and human due to species differences in ascorbate synthesis and plasma and CSF concentrations. To test this, human neuronal cultures were derived from human neural stem cells (hNSC). Unfortunately, because human neurons cannot be grown on glass coverslips, a requirement for quantitative imaging analysis, we were unable to carry out analysis of functional terminal density or to monitor changes in $[Mg^{2+}]_i$. The only option to evaluate effects of threonate on human neurons was to determine the expression of pre- and postsynaptic proteins, which is supposed to be proportional to the number of synapses.

Figure 7B:
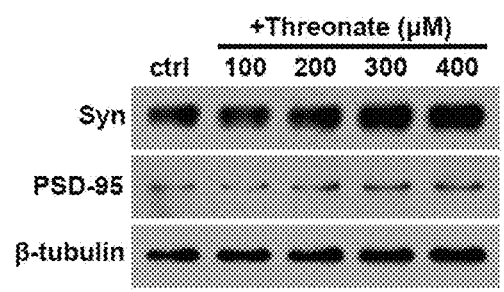
FIGS. 7Aa-7C are a collection of graphs and images showing that elevating threonate increased expression of Syn and PSD-95 in human neurons, according to embodiments of the present disclosure.
Figure 7C:
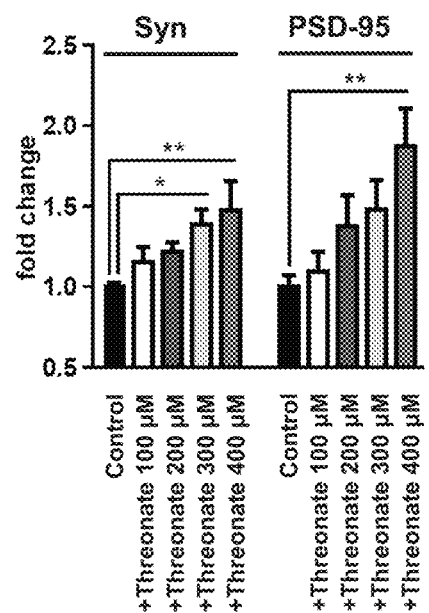

FIG. 7A shows the experimental protocol used for deriving neurons from hNSC. In this cell line, structural and functional synapses are present at day 45 following induction of differentiation. Glutamatergic synapses at day 80 was observed, via fluorescent colocalization of Syn (presynaptic) and PSD-95 (postsynaptic) (FIGS. 7Ac-7Af), and treated the human neurons with threonate at day 90. Similar to our findings in cultured rat hippocampal neurons, threonate treatment significantly increased Syn and PSD-95 expression in a dose-dependent manner (Syn, $F_{4,67}=4.499$, p=0.0028; PSD-95, $F_{4,44}=4.221$, p=0.0056; FIGS. 7B, 7C). Interestingly, compared to the rat dose response curve, in human neurons, the threonate dose response curve was shifted toward a higher concentration, such that even at 400 μM, a concentration higher than human physiological concentration, the effects of threonate continued to increase. This shift seems to be matched with the higher concentration of threonate in human CSF.

FIGS. 7Aa-7C. Elevating Threonate Increased Expression of Syn and PSD-95 in Human Neurons.

(FIG. 7Aa) Schematic of protocol for differentiation of human neural stem cells (hNSC) into neurons and subsequent threonate treatment. (FIG. 7Ab) Neurospheres at optimal size for passaging after proliferation. (FIGS. 7Ac-7Af) Confocal microscopy images of immune-fluorescence staining for hNSC-derived neurons. (FIG. 7Ac) Images of dendrites (MAP2) showing localization of foci of the excitatory synapse. Physical synapses (arrows in f) were identified by juxtaposition of pre- and postsynaptic proteins, either Syn (FIG. 7Ad) or PSD-95 (FIG. 7Ae). (FIGS. 7B-7C) Representative western blot (FIG. 7B) and quantified histogram (FIG. 7C) of Syn (n=9-18) and PSD-95 (n=6-13) in control and threonate treated hNSC-derived neurons. β-tubulin was used as a loading control. Data are presented as fold change relative to control. One-way ANOVA and Bonferroni's post hoc test; *p<0.05; **p<0.01.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A method of increasing brain synaptic density of an individual, comprising:
    administering to an individual a first dosage form comprising an effective amount of a threonate-containing compound, or a precursor thereof, to increase synaptic density in one or more regions of the brain of the individual,
    wherein the threonate-containing compound, or precursor thereof, is not a magnesium salt and the first dosage form is not co-administered with a second dosage form comprising a magnesium-containing compound, wherein the threonate-containing compound, or precursor thereof, is a monovalent, divalent or trivalent cation salt, or precursor thereof, of threonate which is selected from the group consisting of: H+, Li+, Na+, K+, Ca2+, NH44, Ci-C8 monoalkylammonium, C2-C8 dialkylammonium, C3-C8 trialkylammonium, and Fe3+/2+.

2. The method of claim 1, wherein the one or more regions of the brain comprise the hippocampus, cortex, amygdala, and/or the basal ganglion.

3. The method of claim 1, wherein the first dosage form comprises one or more additional agents selected from the group consisting of a pharmacological agent, a flavoring agent, a coloring agent, a sweetening agent, a filling agent, a binding agent, a lubricating agent, an excipient, and a preservative.

4. A method of increasing intracellular magnesium concentration, comprising:
    providing to a medium comprising a cell, a threonate-containing compound, or a precursor thereof, to increase the concentration of threonate in the medium, wherein the increased concentration of threonate is sufficient to increase the concentration of magnesium in the cell compared to the concentration of magnesium in the cell before the providing,
    wherein the threonate-containing compound, or precursor thereof, is not a magnesium salt and no magnesium-containing compounds are provided, wherein the threonate-containing compound, or precursor thereof, is a monovalent, divalent or trivalent cation salt, or precursor thereof, of threonate which is selected from the group consisting of: H+, Li+, Na+, K+, Ca2+, NH44, Ci-C8 monoalkylammonium, C2-C8 dialkylammonium, C3-C8 trialkylammonium, and Fe3+/2+.

5. The method of claim 4, wherein the cell is in vitro, and wherein the providing comprises contacting the cell with a composition comprising the threonate-containing compound, or a precursor thereof.

6. The method of claim 1, wherein the threonate-containing compound, or precursor thereof, is a sodium salt, or precursor thereof, of threonate.

7. The method of claim 1, wherein the method is for maintenance of, or preventing a decline in the cognitive state of the individual.

8. The method of claim 1, wherein the method is for enhancing cognitive function of the individual.

* * * * *